United States Patent
Tomlinson et al.

(10) Patent No.: US 12,172,153 B2
(45) Date of Patent: Dec. 24, 2024

(54) FLOCCULANT FUNCTIONALIZED SEPARATION MEDIA

(71) Applicant: LIFE TECHNOLOGIES CORPORATION, Carlsbad, CA (US)

(72) Inventors: Andrew Tomlinson, Wells, ME (US); Matthew Buchanan, Atkinson, NH (US); Kelly Flook, Bedford, MA (US); Kevin Galipeau, Westford, MA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 1062 days.

(21) Appl. No.: 16/970,444

(22) PCT Filed: Feb. 27, 2019

(86) PCT No.: PCT/US2019/019902
§ 371 (c)(1),
(2) Date: Aug. 17, 2020

(87) PCT Pub. No.: WO2019/169040
PCT Pub. Date: Sep. 6, 2019

(65) Prior Publication Data
US 2021/0170389 A1    Jun. 10, 2021

Related U.S. Application Data

(60) Provisional application No. 62/756,479, filed on Nov. 6, 2018, provisional application No. 62/635,947, filed on Feb. 27, 2018.

(51) Int. Cl.
*B01J 39/05* (2017.01)
*B01D 15/36* (2006.01)
(Continued)

(52) U.S. Cl.
CPC ........... *B01J 39/05* (2017.01); *B01D 15/362* (2013.01); *B01J 39/20* (2013.01); *B01J 47/014* (2017.01); *B01J 47/02* (2013.01); *C07K 1/18* (2013.01)

(58) Field of Classification Search
CPC ............... B01D 15/38; B01D 15/3809; B01D 15/3828; B01D 15/36; B01D 15/362; B01J 39/05; B01J 39/20; B01J 47/014
See application file for complete search history.

(56) References Cited

U.S. PATENT DOCUMENTS

| | | | |
|---|---|---|---|
| 2008/0203029 A1* | 8/2008 | Deorkar | B01J 20/285 210/659 |
| 2011/0201078 A1* | 8/2011 | Rasmussen | C08F 220/56 536/25.4 |

(Continued)

OTHER PUBLICATIONS

International Search Report and Written Opinion for Application No. PCT/US2019/019902, mailed Jul. 29, 2019, 17 pages.

*Primary Examiner* — Yate' K Cutliff

(57) ABSTRACT

Provided herein are compositions, methods and uses that relate to or result from providing separation media having at least one flocculant ligand covalently attached to a base surface or support, and the separation and/or purification of biological molecules using the separation media of the present disclosure. Certain embodiments provide separation media which under certain modes of operation, enhance the separation of the molecule of interest from impurities.

14 Claims, 19 Drawing Sheets

(51) Int. Cl.
*B01J 39/20* (2006.01)
*B01J 47/014* (2017.01)
*B01J 47/02* (2017.01)
*C07K 1/18* (2006.01)

(56) References Cited

U.S. PATENT DOCUMENTS

2011/0217752 A1\* 9/2011 Rasmussen ............ C08G 69/10
   536/25.4
2012/0283419 A1\* 11/2012 Thiyagarajan ....... C07K 5/0215
   530/416

\* cited by examiner

FLOCCULANT FUNCTIONALIZED SEPARATION MEDIA

CROSS-REFERENCE

This application is a 371 of International Application No. PCT/US2019/019902 filed Feb. 27, 2019, which claims the benefit under 35 U.S.C. § 119 (e) of U.S. Provisional Application No. 62/635,947, filed 27 Feb. 2018 and U.S. Provisional Application No. 62/756,479, filed 6 Nov. 2018. The entire contents of the aforementioned applications are incorporated by reference herein.

FIELD OF THE INVENTION

The present disclosure relates to separation media having at least one flocculant ligand as described herein, covalently attached to a base surface or support. The disclosure also relates to separation and/or purification of biological molecules of interest using the separation media of the present disclosure.

BRIEF SUMMARY OF THE INVENTION

The present disclosure is directed, in part, to separation media compositions, methods and systems for the purification and/or separation of biological substances. Specifically, the present disclosure is directed to novel separation media wherein a base surface is functionalized such that a soluble flocculant (flocculant ligand) is immobilized or covalently attached to the base surface. In particular, the present disclosure is based on the surprising observation that, the immobilized flocculant separation media generated therein, dramatically improved the removal of impurities, for e.g., high molecular weight and low molecular weight species (including antibody aggregates) due to their selective binding of impurities, under certain conditions also described herein. It has also been surprisingly discovered that the separation media described herein are capable of separating monomers of a biological molecule from aggregates across a wide range of pH and across a wide range of conductivity.

In one embodiment, the disclosure provides a separation medium comprising:
  a. a base surface; and
  b. at least one flocculant ligand covalently attached to the base surface.

In another embodiment, the disclosure provides that the at least one flocculant ligand is selected from the group consisting of cationic, anionic, non-ionic and natural flocculants.

In another embodiment, the anionic flocculant further comprises an unsubstituted or substituted aliphatic carboxylic acid, an unsubstituted or substituted aromatic carboxylic acid, an unsubstituted or substituted aliphatic sulfonic acid, an unsubstituted or substituted aliphatic acrylic acid, an unsubstituted or substituted aliphatic thiosulfate, an unsubstituted or substituted aliphatic phosphonic acid, or an unsubstituted or substituted aliphatic phosphoric a fatty acid.

In another embodiment, the unsubstituted or substituted aliphatic groups are either linear or branched, and optionally, comprise one or more double bonds.

In another embodiment, the unsubstituted or substituted aliphatic groups have from 1 to about 30 carbon atoms, preferably from 1 to about 20 carbon atoms, more preferably from about 1 to about 10 carbon atoms, most preferably from about 1 to about 8 carbon atoms.

In another embodiment, the unsubstituted or substituted aliphatic group is a $C_1$-$C_8$ aliphatic acid.

In another embodiment, the unsubstituted or substituted aliphatic group is a $C_9$-$C_{30}$ aliphatic acid.

In another embodiment, the separation medium is contacted with a solution, a feed or an eluent that comprises one or more ligate species, under operating conditions that allow the binding of at least one ligate species from the solution, feed or eluent, to the separation medium.

In another embodiment, the one or more ligate species is a mixture of biological substances.

In another embodiment, the mixture of biological substances comprises a target molecule and at least one impurity.

In another embodiment, the impurity is an aggregate, or is a product related impurity, or is a process related impurity.

In another embodiment, the target molecule is either a monomeric antibody, a therapeutic peptide or protein, a virus or viral particle, a particular variant of a peptide or protein or antibody or virus or viral particle, or a nucleic acid.

In another embodiment, an aggregate is made of: several antibody monomers, antibodies with higher levels of post translational modifications, an antibody monomer in combination with one or more of the following: an antibody light chain, host cell protein (HCP), protein or viral fragment, antibody fragment, viruses or viral particle, cell culture impurity, cell debris, cell culture media component, other unwanted species.

In another embodiment, the at least one target molecule is an antibody monomer, and the at least one impurity is an aggregate.

In another embodiment, the separation medium selectively binds an aggregate, and wherein the separation medium has a separation factor ($\alpha$) of greater than 1.

In another embodiment, the antibody monomer is separated from one or more aggregates with the separation factor ($\alpha$) of at least about 1.5, preferably of at least about 2.5, more preferably of at least about 4.0.

In another embodiment, the antibody monomer is separated from one or more aggregates with the separation factor ($\alpha$) of about 1.1 to about 11.

In another embodiment, the separation medium is capable of separating an antibody monomer from the aggregate after single contact with the separation medium.

In another embodiment, the antibody monomer purity is >90% after contact with the separation medium.

In another embodiment, the antibody monomer recovery is >85% after contact with the separation medium.

In another embodiment, the antibody monomer purity is from about 95 to about 100%, or preferably, from about 98 to about 100%.

In another embodiment, the antibody monomer recovery is from about 85% to about 100%, or preferably, from about 90% to about 100% after contact with the separation medium.

In another embodiment, the antibody monomer is purified in flow-through mode.

In another embodiment, the separation medium selectively binds an antibody monomer, and wherein the separation medium has a separation factor ($\alpha$) of less than 1.

In another embodiment, the antibody monomer is separated from one or more aggregates with the separation medium having a separation factor ($\alpha$) of at least about 0.1 to about 0.9, preferably of at least about 0.3 to about 0.9, most preferably of at least about 0.6 to about 0.9.

In another embodiment, the antibody monomer is purified in bind-elute mode.

In another embodiment, the cationic flocculant ligand is either a primary aliphatic amine, a secondary aliphatic amine, a tertiary aliphatic amine, an aliphatic imine, an aliphatic hydrazide, an imidazole, an aliphatic oxime, an aliphatic hydrazine, an aliphatic hydrazone, a linear polyethyl amine, a polyethyleneimine, a heterocyclic quaternary ammonium, or a cationic polyelectrolyte.

In another embodiment, the cationic flocculant ligand is selected from the group consisting of tris(2-aminoethyl) amine, tris(3-aminopropyl)amine, polydiallyldimethylammonium chloride (PolyDADMAC) and poly(N,N-dimethylpiperidinium chloride), poly(N-vinylpyrrolidone) (PVP), copolymers of poly(ethyleneimine), and quaternary aminated polyacrylates.

In another embodiment, the separation medium can selectively bind to an impurity, and/or, wherein the impurity is a nucleic acid.

In another embodiment, the separation medium can selectively bind to impurities, and/or, wherein the charged variant are is a glycosylated, a glycated, an oxidized, a deaminated, an acidic, a basic, a phosphorylated, a sialylated or a N-terminal acetylated form.

In another embodiment, the at least one non-ionic flocculant ligand is either a styrene, substituted styrene, polymeric styrenes, an uncharged aliphatic, an uncharged branched aliphatic, a hydrophobic polyester, a hydrophilic polyester, a polyacrylamide, a poly(ethylene oxide), or copolymers thereof.

In another embodiment, the flocculant natural ligand is either a polysaccharide, an amino, imino, ammonium, sulfonium or phosphonium functionalized polysaccharide, a collagen, an anionic protein, a cationic protein, a chitosan, an iningláss, guar gum, a cationic protein from Moringa oleifera seeds or Strychnos potatorum seeds, or an alginate.

In another embodiment, the base surface includes but is not limited to: a resin, bead, sphere, particle, microcarrier, membrane, web, bag, bioreactor, tube, plate, array, flat surface, filter, fiber or a fabric.

In another embodiment, the base surface is porous, nonporous, microporous, woven, non-woven, polymeric, non-polymeric, fibrous or winged.

In another embodiment, the base surface is made up of materials including but not limited to: ceramics, glass, metal, silica, synthetic polymeric materials such as styrenic, acrylate, acrylamide, acrylamide containing one or more polymerizable vinyl groups, polymeric monoliths, etc., natural polymers such as cellulose, lignocellulose or their derivatives, agarose, or a combinations of any of these materials.

In another embodiment, the separation medium is contacted with a solution, a feed or eluent comprises one or more ligate species, under operating conditions that allow the binding of at least one ligate species to the separation medium.

In another embodiment, the ligate species is a mixture of biological substances.

In another embodiment, the mixture of biological substances comprises a target molecule and at least one impurity.

In another embodiment, the impurity is either a product related impurity or a process related impurity.

In another embodiment, the target molecule is either a monomeric antibody, a therapeutic peptide or protein, a virus or viral particle, a particular variant of a peptide or protein or antibody or virus or viral particle, or a nucleic acid.

In another embodiment, an aggregate is made of: several antibody monomers, antibodies with higher levels of post translational modifications, an antibody monomer in combination with one or more of the following: an antibody light chain, host cell protein (HCP), protein or viral fragment, antibody fragment, viruses or viral particle, cell culture impurity, cell debris, cell culture media component, other unwanted species.

In another embodiment, the at least one target molecule is an antibody monomer, and the at least one impurity is an aggregate.

In another embodiment, the separation medium is capable of separating a monomer and at least one aggregate in a pH range of about 2 to about pH 11.

In another embodiment, the separation medium is capable of separating a monomer and at least one aggregate in a solution having a conductivity of about 1 mS/cm to about 200 mS/cm.

In a certain embodiment, a chromatography system comprising; a column, and, enclosed within the column, a separation medium as described above, is described.

In another embodiment, the system comprises a pump for passing a liquid through the separation medium at a velocity of about 50 to about 1000 cm/hr, wherein the liquid is a solution, an eluent, or a feed comprising one or more biological substances.

In yet another embodiment, a method of separating a monomer and least one aggregate comprising;
i. providing a separation medium described above; and
ii. passing a solution, an eluent, or a feed comprising one or more biological substances through the separation medium at a rate sufficient to allow at least one soluble molecule to bind to the separation medium, is described.

In another embodiment, the biological substance in the flow-through fraction is collected.

In another embodiment, the biological substance in the flow-through fraction is an antibody monomer.

In another embodiment, the biological substance in the flow-through fraction is an impurity.

In another embodiment, the antibody monomer purity is >90% after contact with the separation medium, or preferably, the antibody monomer purity is at least about 95% to at least about 100%, or more preferably, from at least about 98% to at least about 100% purity.

In another embodiment, the antibody monomer purity is at least about 95% to at least about 100%, or more preferably, from at least about 98 to at least about 100% purity; and/or, the antibody monomer recovery is at least about 85% to about 100%, or preferably, from at least about 95% to about 100% recovery after contact with the separation medium.

In another embodiment, the method further comprises: iii. eluting one or more bound biological substance to provide a plurality of fractions. In a further embodiment, the method further comprises:
iv. analyzing the fractions by size exclusion chromatography.

In another embodiment, the step of passing the solution is carried out at a pH of about 2 to about 11.

In another embodiment, the step of passing the solution is carried out at a conductivity of about 1 mS/cm to about 200 mS/cm.

In another embodiment, the method further comprises regenerating the separation medium.

In a certain embodiment, a method of purifying a protein of interest from a solution, an eluent, or a feed comprising:

i. providing a separation medium, as disclosed herein, and ii. passing the solution, eluent, or feed comprising the protein of interest and one or more impurities through the separation medium at a rate sufficient to allow the one or more impurities to bind to the separation medium, is described.

In another embodiment, the protein of interest is in the flow-through fraction.

In another embodiment, the protein of interest is an antibody monomer.

In another embodiment, the antibody monomer purity is at least about 95% to at least about 100%, or more preferably, from at least about 98 to at least about 100% purity; and/or, the antibody monomer recovery is at least about 85% to about 100%, or preferably, from at least about 90% to about 100% recovery after contact with the separation medium.

In another embodiment, the solution, eluent, or feed is a spent cell culture fluid, a solution containing proteins, or a biological fluid.

In another embodiment, the culturing is performed in a flask, a plate, a well, an array, a bioreactor, a disposable container, or a bag.

In another embodiment, at least about 90% to about 100% of an impurity is removed.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6b is the fraction from commercial AEX resins POROS XQ (control, non-flocculant AEX resin); FIG. 6c is from POROS HQ (control, non-flocculant AEX resin); FIG. 6d is from AEX resin 1; and FIG. 6e is from AEX resin 2.

In FIG. 6a, the chromatographic panel shows the variant profile of ovalbumin when injected onto and separated using an analytical HPLC column.

DETAILED DESCRIPTION OF THE INVENTION

Figure 1A:
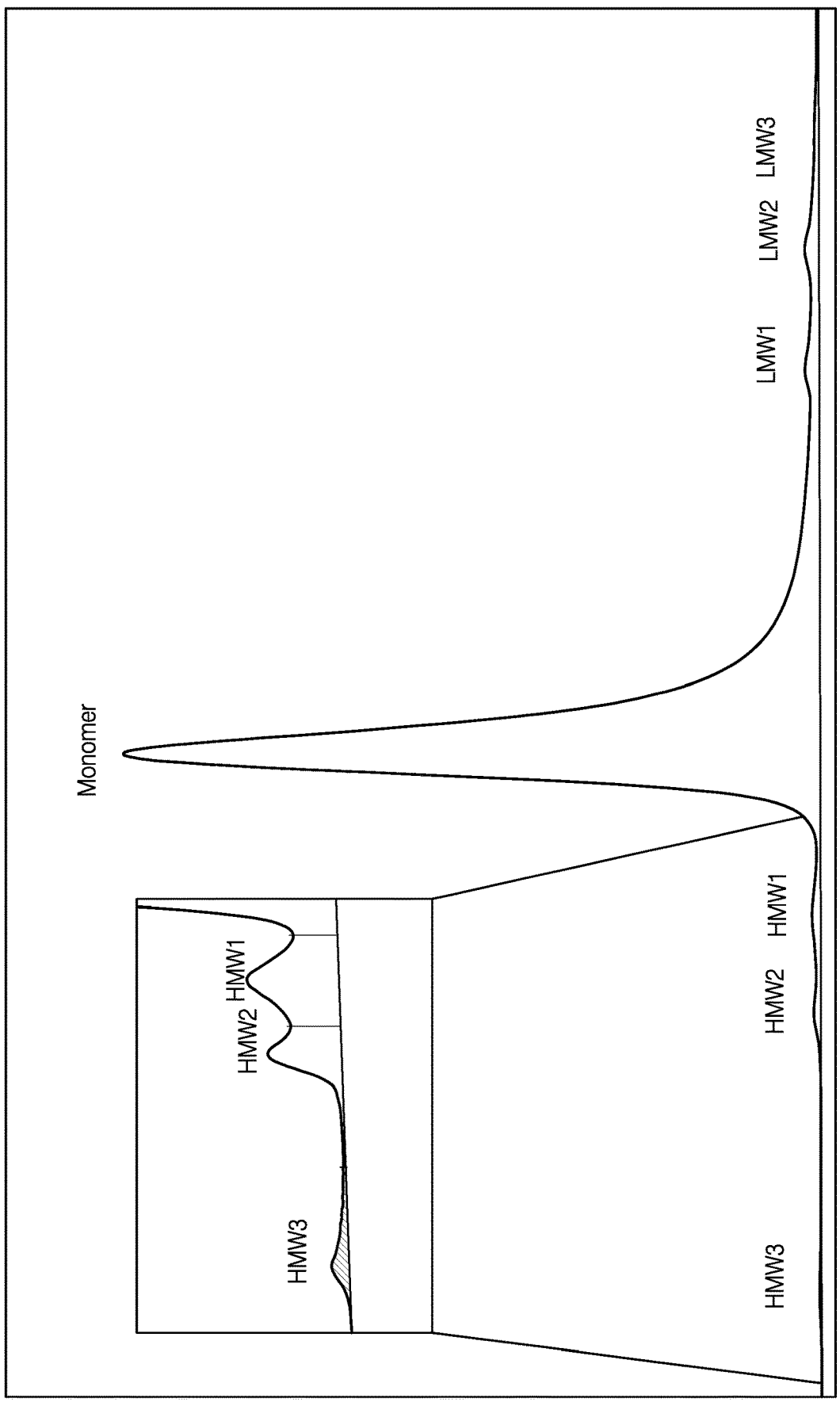
FIG. 1a: The Size Exclusion Chromatography (SEC) profile of an antibody input sample (feed) after protein A column purification is shown. The purity of the SEC feed is about 90-95% pure, but the antibody monomer (target molecule) still contains impurities like high molecular weight (HMW) and low molecular weight (LMW) aggregate species (the species peaks are labeled as 1, 2, 3). These need to be separated out. In one embodiment, the exemplary novel separation media described in the present disclosure provide unique features that enable the effective removal of HMW and LMW from a given sample or feed.

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations and embodiments pertaining to the elements of the compositions or methods described herein are specifically enumerated by the present disclosure and are disclosed herein just as if each and every combination was individually and explicitly disclosed; to the extent that such combinations are not in conflict with one another. In addition, all subcombinations of the elements of the compositions or methods described herein are also specifically enumerated by the present disclosure and are disclosed herein just as if each and every sub-combination was individually and explicitly disclosed herein; to the extent that such sub-combinations are not in conflict with one another.

Definitions

In describing certain embodiments of the present disclosure:

"Base surface or support" includes but are not limited to: resins, beads, spheres, particles, microcarriers, membranes, webs, bags including single use bags, bioreactors, tubes, plates, arrays, flat surfaces, filters, fibers, fabrics, etc. Each type of supports described herein can be porous, non-porous or microporous, woven or non-woven, polymeric or non-polymeric, fibrous or winged. A support or surface can be made of a variety of materials, including but not limited to: ceramics, glass, metal, silica, synthetic polymeric materials such as styrenic, acrylate, acrylamide, vinyl, polymeric monoliths, etc., natural polymers such as cellulose, lignocellulose or its derivatives, agarose, for e.g., Sepharose™, or a combinations of such materials.

"Flocculant" means a chemical entity that induces, or has the potential to cause, precipitation of biological materials such as a "target molecule" described herein upon contact with the flocculant. Without being bound by theory, flocculants are thought to hold to the biological material being precipitated by weak physical interactions, which may ultimately lead to separation. Exemplary flocculants described include but are not limited to: cationic flocculants, anionic flocculants, non-ionic flocculants, natural flocculants, and combinations thereof, as will be described further below.

A "flocculant ligand" is generated when a flocculant or a flocculant-like chemical entity is covalently attached, coupled, immobilized or functionalized on to any base surface or a support described above. Once of skill in the art would know to use a suitable reactive functional group on the base surface or support to attach the flocculant ligand. Without being bound by theory, the immobilized flocculant or flocculant-like ligand is thought to interact with a biological species (the "ligate") in solution, reversibly, by ionic, hydrophobic, hydrogen-bonding, or a combination of these type of interactions.

"Separation medium" means a base surface or support that is functionalized with a flocculant or a flocculant-like ligand. In a preferred embodiment, a separation medium (for e.g., a flocculant functionalized resin) is part of a chromatography system comprising; a column, and, separation medium, for e.g., a resin, is enclosed within the column.

"Ligate" means any molecule or species which can interact, in a reversible manner, with a support comprising the immobilized flocculant or the flocculant-like ligand. "Binding" refers to the interaction of the ligate with the immobilized flocculant or the flocculant-like ligand; this is generally a reversible reaction which can be disrupted by changes in pH, ionic strength, etc., of the solution. Depending on the mode of operation, sometimes, the "target molecule," described herein, may be the "ligate". At other times, the "impurity" may be the "ligate".

"Target" or "target molecule" means any molecule of interest. For e.g., the target molecule is the molecule that needs to be purified, concentrated, or separated, or isolated, or enriched. In certain embodiments, the target molecule is a biological molecule of interest, for e.g., antibodies, proteins; peptides; glycoproteins; lipoproteins, enzymes, nucleic acids (RNA, DNA, etc.); nucleoproteins; viruses; viral fragments; viral capsids; viral antigens; antigenic proteins; cellular markers; cells or particular cell types—for e.g., certain types of T cells; a cellular component or cell parts; organelles and the like; receptor proteins; vaccines; etc. In certain embodiments, the "target molecule" of interest may have pharmaceutical, diagnostic, agricultural, and/or any of a variety of other properties that are useful in commercial, experimental or other applications. In addition, a "target molecule" of interest can be an antibody or protein therapeutic. In certain embodiments, proteins produced may be processed or modified. For example, a protein may be glycosylated. In exemplary embodiments, the "target molecule" is an antibody. In a preferred embodiment, the "target molecule" is a monomeric antibody.

In other embodiments, the "target molecule" can be an enzyme, such as lysozyme, chymotrypsinogen, ribonuclease A, and the like; or a protein, such as bovine serum albumin (BSA), cytochrome C, and the like.

"Impurity" or "contaminant" means any unwanted ligate species other than the "target molecule". Generally, any undesired products in the mixture, may include aggregates as described below, host cell proteins (HCP), host cell metabolites, antibody fragments, protein fragments, nucleic acids, endotoxins, viruses or viral particles or viral protein fragments, other impurities from cell culture such as cells and their fragments, cell culture media components, media additives, media derivatives, product related contaminants, lipids, etc. Certain contaminants may first be removed by initial steps including, but not limited to, centrifugation, sterile filtration, depth filtration or tangential flow filtration.

"Impurities" also mean 'product related impurities' which include but are not limited to charge variants of the target molecule, truncated forms, or aggregates of the molecules (e.g., dimers, trimers, etc.). Charge variants may include but are not limited to glycosylated, glycated, oxidized, deaminated, acidic, basic, phosphorylated, sialylated or a N-terminal acetylated forms, of the desired target molecule. Impurities could also mean 'process related impurities' which include but are not limited to: host cell proteins, nucleic acids, aggregates (precipitates, cell debris, media components, fragments, etc.).

"Aggregate" can be "high molecular weight species" (HMW) or a "low molecular weight species" (LMW). When used in antibody purification, antibody "aggregates" refer to higher molecular forms of an antibody formed due to the aggregation of one or more monomeric antibodies into dimers, trimers, tetramers, etc. An aggregate may comprise multiple monomers of the desired antibody in the antibody aggregate, or, it may comprise additional antibody light chains, or antibodies with a higher level of post translational modifications, or aggregated host cell proteins (HCP), or aggregated antibody plus protein fragments, or a combination of antibody monomer with one or more contaminants including antibody fragments, protein fragments, host cell proteins (HCP), viruses or viral particles or viral protein fragments, other impurities from cell culture such as cells and their fragments, cell culture media components, or other unwanted ligate species. HMW impurities can include aggregates (dimers, trimers, tetramer etc., and/or, antibody monomer with a light chain, and/or antibody with high levels of post translational modifications, and/or aggregated host cell proteins (HCP), and/or aggregated antibody or protein fragments. Aggregates can also be "low molecular weight species" (LMW) impurities such as host cell proteins (HCP) or antibody fragments or protein fragments.

The term "antibody" is used in the broadest sense to cover monoclonal antibodies (including full length monoclonal antibodies), polyclonal antibodies, multispecific antibodies (e.g., bispecific antibodies), antibody fragments, immunoadhesins and antibody-immunoadhesin chimerias. An antibody may include, for example, an antibody of any molecule class, e.g., $IgG_1$, $IgG_2$, etc. that is to be purified from a mixture containing contaminants. An "antibody fragment" includes at least a portion of a full length antibody and typically, an antigen binding or variable region thereof; for e.g., they include Fab, Fab', $F(ab')_2$, and Fv fragments; single-chain antibody molecules like camelid antibodies; diabodies; linear antibodies; and multispecific antibodies formed from engineered antibody fragments. The term "monoclonal" antibodies, indicates the character of the antibody as being obtained from a substantially homogeneous population of antibodies, and is not to be construed as requiring production of the antibody by any particular method. The monoclonal antibodies described herein include "chimeric" and "humanized" antibodies, and "human" antibodies, which can be isolated from various sources, including, e.g., from the blood of a human patient or recombinantly prepared using transgenic animals.

"Monomer" in the context of antibodies, refers to a monomeric antibody. However, "monomer" in a non-antibody context, may mean the monomeric form of any biological molecule of interest (target), say, of a heteromeric protein or enzyme.

"Selectivity" is a term that is used to describe the preferential binding of one ligate species over another on any base surface. Selectivity can also be expressed as a separation factor ($\alpha$), which is a measure of the preferential selectivity of a separation medium for either an impurity or a target molecule, depending on the operating conditions.

Separation factor $(\alpha) = K_p$ impurity/$K_p$ target molecule.

In a certain embodiment, the target molecule is an antibody monomer, and the impurity is an "aggregate". This embodiment is also seen in Example 1 where Equation 1 is also expressed as, Separation factor $(\alpha) = K_p$ aggregate/$K_p$ monomer.

Under certain modes of operation, $(\alpha) > 1$, which means that under these operating conditions, the separation medium preferentially binds the impurity, and correspondingly, the target molecule will bind less or not at all (i.e., in a column chromatography setting, the target molecule will flow through). Under other modes of operation, $(\alpha) < 1$, which means that the operating conditions are selective for, and preferentially binds the target molecule, and correspondingly, impurities will bind less or not at all to the separation medium (in column chromatography, the impurity will flow through).

In a certain embodiments, selectivity describes the separation of solutes in a chromatographic run, and refers to the overall chromatographic profile (retention time, separation, elution order, etc.) for a series of ligates.

"Recovery" refers to the amount of purified ligate material obtained compared to the amount of ligate available in the original feed. In a certain embodiment, recovery is the amount of purified ligate capable of being eluted from a chromatographic column relative to the amount of ligate available in the original feed.

DETAILED DESCRIPTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Bringing downstream operations closer or into the bioreactor has significant advantages for reduction of purification steps in processes. To this end there have been reports of use of flocculants for specific removal of process contaminant such as host cell proteins while maintaining target biomolecules such as a monoclonal antibody in solution. Molecules such as organic acids, caprylic acid also known as octanoic acid, synthetic polymers such as polyethyleneimmine (PEI), and polydiallyldimethylammonium chloride (PolyDADMAC), polysaccharides such as chitosan, sodium alginate, cellulose, lignin, tannin, etc. and other known flocculants across many industries may be used, alone or in a suitable combination, for such purposes. In addition to removal of host cell proteins, use of flocculants may also cause reduction of product related impurities such as aggregates and may under certain conditions lead to the inactivation of viruses. Resulting harvests are of reduced complexity and lead to simplified purification operations and potentially a reduced number of operations to product molecules of sufficient purity for human therapeutic use.

Soluble caprylic acid (CA) has been used as a flocculant to flocculate proteins. For instance, a method for a purifying protein of interest using soluble CA (not immobilized) is described in US application US20120101262A, hereby incorporated by reference in its entirely. However, there are some disadvantages in using soluble caprylic acid (CA). The final concentration of soluble caprylic acid used to the purification mixture was generally between about 0.05 and 5% (v/v), or in certain embodiments, the contaminant precipitate is allowed to form between soluble CA and target protein for between about 30 to 120 minutes after addition of the caprylic acid (e.g., between about 30 to 60 minutes). Due to the hydrophobic character of CA, it may bind to the antibody protein of interest and be carried through the purification process as a contaminant. Hence, additional steps may be needed to remove the contaminating CA accompanying the target protein of interest in the final purification step. Further, the pH of the solution needs to be adjusted to less than pH 5 prior to adding soluble CA, which might cause antibody aggregation thereby increasing the number of impurities in the end-product.

Caprylic acid has also been used as a wash solution in chromatography operations to specifically remove or precipitate process and product impurities before elution of the target molecule. However, its relatively poor solubility in aqueous solution limits the operation ranges within manufacturing processes. Additionally, temperature fluctuations as might be encountered during transfer of manufacturing operations from one plant to another across the globe, challenges process robustness through changing solubility.

In the present disclosure, the CA (and other flocculants described herein) are surface bound (immobilized); which means that a flocculant like CA need not be removed, or the CA/or flocculants have a far lesser chance of contaminating the target protein of interest. In a surprising result, it has been discovered that the compositions and methods of this disclosure employing immobilized flocculants are capable of separating proteins of interest from impurities. For example, it will be demonstrated in this disclosure that an antibody monomer can be separated from an impurity (aggregate) efficiently, to a greater degree and purity and with greater recovery than previously known with commercial separation products and methods.

In addition, purification may be achieved faster and with lesser quantities per volume of CA, presumably since the flocculant is bound to resin. Furthermore, the mixing time for the binding is faster, almost instantaneous, with bound CA. Still further, the pH adjustment step needed during soluble flocculation is not needed with bound flocculant or caprylic acid. Given these advantages, this disclosure proposes the preparation of immobilized flocculant surfaces which include, the immobilization of anionic flocculants, cationic flocculants, non-ionic flocculants and natural flocculants onto any surface.

The disclosure relates to immobilization of a molecule typically used as a flocculent to the surface of a solid support. In another embodiment, the disclosure provides a separation medium comprising a base surface; and at least one flocculant ligand covalently attached to the base surface. In another embodiment, the disclosure provides a chromatography system comprising a column, and, enclosed within the column, a separation medium comprising a base surface; and at least one flocculant ligand covalently attached to the base surface. The separation media described herein can be used in methods for the separation or purification of a target molecule, such as a biological molecule, from contaminants in a mixture. In some embodiments, the separation media described herein are provided in a system, such as a chromatography system comprising a column, and, enclosed within the column, a separation medium as described herein.

Support or Surfaces for Immobilization

In the present disclosure, a range of flocculant ligands are immobilized on a surface to generate separation media. The proposed solution was to immobilized surfaces with cationic flocculant ligands, anionic flocculant ligands, non-ionic flocculant ligands and natural flocculant ligands. If any given ligand (cationic, anionic, non-ionic or natural) identified for immobilization is not a flocculant in its soluble form, the present disclosure does not encompass the non-flocculant molecule.

In one embodiment, the flocculant ligand is an "anionic flocculant ligand" that is an aliphatic compound comprising an unsubstituted or substituted aliphatic carboxylic acid, an unsubstituted or substituted aromatic carboxylic acid, an unsubstituted or substituted aliphatic sulfonic acid, an unsubstituted or substituted aliphatic acrylic acid, an unsubstituted or substituted aliphatic thiosulfate, an unsubstituted or substituted aliphatic phosphonic acid, or an unsubstituted or substituted aliphatic phosphoric a fatty acid. In one embodiment, the unsubstituted or substituted aliphatic groups are either linear or branched, and optionally, comprises one or more double bonds. In another embodiment, the unsubstituted or substituted aliphatic groups may have from 1 to about 30 carbon atoms, preferably from 1 to about 20 carbon atoms, more preferably from about 1 to about 10 carbon atoms, most preferably from about 1 to about 8 carbon atoms.

In some embodiments, the flocculant ligand can be an aliphatic acid, a branched aliphatic acid, or a substituted aliphatic acid, each having from 1 to about 30 carbon atoms. In some embodiments, the flocculant ligand can be a fatty acid. In some embodiments, the flocculant ligand can be an optionally substituted $C_1$-$C_8$ aliphatic acid. In some embodiments, the flocculant ligand can be an optionally substituted $C_9$-$C_{30}$ aliphatic acid. In some embodiments, the flocculant ligand can be an optionally substituted $C_1$-$C_3$ aliphatic acid. In some embodiments, the flocculant ligand can be an optionally substituted $C_3$-$C_6$ aliphatic acid. In some embodiments, the flocculant ligand can be an optionally substituted $C_6$-$C_{10}$ aliphatic acid. In some embodiments, the flocculant ligand can be an optionally substituted $C_{10}$-$C_{15}$ aliphatic acid. In some embodiments, the flocculant ligand can be an optionally substituted $C_{15}$-$C_{20}$ aliphatic acid. In some embodiments, the flocculant ligand can be an optionally substituted $C_{20}$-$C_{30}$ aliphatic acid.

In some embodiments, the flocculant ligand can be an arylalkyl compound comprising at least one substituent group, such as an amine or a carboxylic acid, that is capable of providing flocculant properties to the compound. In some embodiments, the substituent group can be a cationic group, an anionic group, or a non-ionic group. In some embodiments, the flocculant ligand can be an arylalkyl compound having from 1 to about 30 carbon atoms comprising at least one substituent group, such as an amine or a carboxylic acid, that is capable of providing flocculant properties to the compound. In some embodiments, the flocculant ligand can be an optionally substituted $C_1$-$C_8$ arylalkyl comprising at least one substituent group, such as an amine or a carboxylic acid, that is capable of providing flocculant properties to the compound. In some embodiments, the flocculant ligand can be an optionally substituted $C_9$-$C_{30}$ arylalkyl compound comprising at least one substituent group, such as an amine or a carboxylic acid, that is capable of providing flocculant properties to the compound. In some embodiments, the flocculant ligand can be an optionally substituted $C_1$-$C_3$ arylalkyl compound comprising at least one substituent group, such as an amine or a carboxylic acid, that is capable of providing flocculant properties to the compound. In some embodiments, the flocculant ligand can be an optionally substituted $C_3$-$C_6$ arylalkyl compound comprising at least one substituent group, such as an amine or a carboxylic acid, that is capable of providing flocculant properties to the compound. In some embodiments, the flocculant ligand can be an optionally substituted $C_6$-$C_{10}$ arylalkyl compound comprising at least one substituent group, such as an amine or a carboxylic acid, that is capable of providing flocculant properties to the compound. In some embodiments, the flocculant ligand can be an optionally substituted $C_{10}$-$C_{15}$ arylalkyl compound comprising at least one substituent group, such as an amine or a carboxylic acid, that is capable of providing flocculant properties to the compound. In some embodiments, the flocculant ligand can be an optionally substituted $C_{15}$-$C_{20}$ arylalkyl compound comprising at least one substituent group, such as an amine or a carboxylic acid, that is capable of providing flocculant properties to the compound. In some embodiments, the flocculant ligand can be an optionally substituted $C_{20}$-$C_{30}$ arylalkyl compound comprising at least one substituent group, such as an amine or a carboxylic acid, that is capable of providing flocculant properties to the compound.

In some embodiments, the cation exchange separation medium (cationic flocculants) described herein can be represented by the following diagrams:

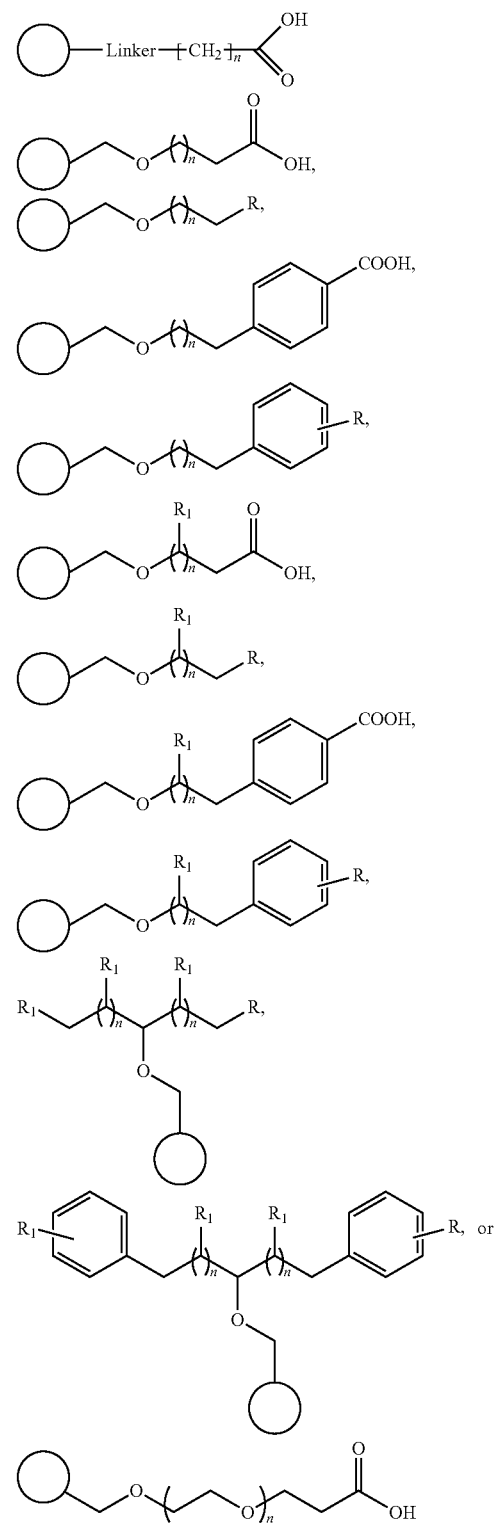

wherein the spheres represent solid supports as defined herein, R can be a functional group as described above, such as a carboxylic acid, amine, sulfonic acid, phosphonic acid, and the like, R1 can be H or a substitutent, such as $C_1$-$C_{20}$ alkyl, $C_6$-$C_{10}$ aryl, carboxylic acid, amine, sulfonic acid, phosphonic acid, hydroxyl, thiol, carbonyl, and the like, and n can be from 0 to about 30.

In another embodiment, the flocculant ligand is a "cationic flocculant ligand" that is an aliphatic primary aliphatic amine, a secondary aliphatic amine, a tertiary aliphatic amine, an aliphatic imine, an aliphatic hydrazide, an imidazole, an aliphatic oxime, an aliphatic hydrazine, an aliphatic hydrazone, a linear polyethyl amine, a polyethyleneimine, a heterocyclic quaternary ammonium, or a cationic polyelectrolyte, a branched aliphatic primary, secondary, or tertiary amine, or a substituted aliphatic primary, secondary, or tertiary amine, each having from 1 to about 30 carbon atoms. In some embodiments, the flocculant ligand can be an optionally substituted $C_1$-$C_8$ aliphatic primary, secondary, or tertiary amine. In some embodiments, the flocculant ligand can be an optionally substituted $C_9$-$C_{30}$ aliphatic primary, secondary, or tertiary amine. In an exemplary embodiment, the cationic flocculant resins is antimicrobial in nature.

Exemplary "cationic flocculant ligands" or polymers include but are not limited to, Tris(2-aminoethyl)amine, Tris(3-aminopropyl)amine, linear polyethyl amines of varying chain lengths, and polyethyleneimine, poly(N-vinylpyrrolidone) (PVP), quaternary aminated polyacrylates, poly (N,N-dimethylpiperidinium chloride), polydiallyldimethylammonium chloride (PolyDADMAC), copolymers of poly(ethyleneimine), and quaternary aminated polyacrylates, etc. Other potential solutions include antimicrobials from the personal care industry, like Triclosan can also be used as cationic flocculants.

In some embodiments, the anion exchange separation medium (anionic flocculant) described herein can be represented by the following diagram:

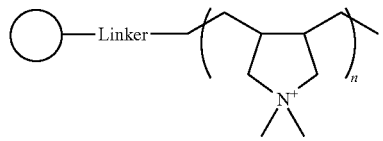

In some embodiments a non-ionic flocculant ligand is immobilized to a base surface, and it can either be a styrene, substituted styrene, polymeric styrenes, an uncharged aliphatic, an uncharged branched aliphatic, a hydrophobic polyester, a hydrophilic polyester, a polyacrylamide, a poly (ethylene oxide), or copolymers thereof.

In other embodiments, a natural flocculant ligand is immobilized on a base surface, and it can either be a polysaccharide, an amino, imino, ammonium, sulfonium or phosphonium functionalized polysaccharide, a collagen, an anionic protein, a cationic protein, a chitosan, an ininglass, guar gum, a cationic protein from Moringa oleifera seeds or Strychnos potatorum seeds, or an alginate.

Solid Surface

In some embodiments, the base surface can be a solid support having a format known to one of ordinary skill in the art. It will be appreciated that each format provided herein for a base surface comprises a solid support. For example, the base surface may include but is not limited to: a resin, bead, sphere, particle, microcarrier, membrane, web, bag, bioreactor, tube, plate, array, flat surface, filter, fiber or a fabric. In a certain embodiment, the base surface may be porous, non-porous, microporous, woven, non-woven, polymeric, non-polymeric, fibrous or winged.

Exemplary base surfaces may include, but are not limited to, chromatographic resins, membranes, porous beads, porous monoliths, winged fibers, woven fabrics, non-woven fabrics, silica, Sepharose™, porous polyvinylether polymeric beads, non-porous beads and their derivatives, styrenic beads and their derivatives, acrylate beads and their derivatives, acrylamide containing one or more polymerizable vinyl group, and the like. It will be appreciated by one of ordinary skill in the art that the base surfaces provided herein are merely exemplary, and that the identity of the base surface is not particularly restricted. It will be further appreciated that base surfaces useful in connection with the present teachings include any base surface that is capable of being modified according to the methods described herein.

Exemplary base surface may be made up of materials including but not limited to: ceramics, glass, metal, silica, synthetic polymeric materials such as styrenic, acrylate, acrylamide, acrylamide containing one or more polymerizable vinyl groups, polymeric monoliths, etc., natural polymers such as cellulose, lignocellulose or their derivatives, agarose, or a combinations of any of these materials. Examples of suitable base surfaces include, but are not limited to those describes in U.S. Pat. Nos. 5,334,310, 5,453,185, 5,593,729, 5,728,457, 5,929,214, 6,238,565, 6,616,825, 5,833,861, 5,605,623, 5,552,041, 8,940,172, 3,997,482, 8,356,717, 9,028,683, US Patent Application Publication No. 20100160605 A1, US Patent Application Publication No. 20140073769 A1, US Patent Application Publication No. 20130245139 A1, US Patent Application Publication No. 20020043499 A1, and US Patent Application Publication No. 20140316017 A1, the disclosures of each of which are incorporated herein by reference with respect to their disclosure related to solid supports and methods of making solid supports, to the extent that such teachings are not in conflict with the present disclosure.

Reactivity on the Support or Surface

In order to be useful for the purposes of the disclosure, the support must be a reactive support and that reactive group should be capable of undergoing rapid, direct covalent coupling with a given flocculant or flocculant-like chemical entity to form the "flocculant ligand" or result in flocculant derivatized supports. In an exemplary embodiment described in Example 1, surface hydroxyl groups on the base resin react in an SN2 reaction.

In general, for coupling, one end of the reaction would comprise a nucleophilic group while the other end would comprise an electrophilic (leaving) group. Useful reactive leaving groups or electrophiles, include halides (for e.g., bromine and chlorine), tosylate, mesylate, esters including NHS esters, carbonates, carbamates and the like. One of skill in the chemical arts would understand that the nucleophile-electrophile pair, or entities could be either on the base surface or on the "flocculant ligand", but the nucleophile-electrophile entities must be present for the reaction to occur or for covalent coupling to occur.

Shown here are some exemplary reactions for the coupling of flocculant ligands or a given base surface: for example, one can also perform reductive amination with an amine moiety at one end and an aldehyde on another end. Or, in situ activation of a carboxylic acid on a surface to form an NHS moiety, and react it with amine on a "flocculant ligand" containing an amine. Or, epoxide on one surface can react with OH, NH2 or SH on the other. Or, one can link NH2 on both surfaces with bis NHS as a linker (see for example, U.S. Pat. No. 9,139,667). Or, an aldehyde on one end can react with hydrazine, hydrazide, or aminoxy (hydroxylamine) on other end. Or, sufonylchloride on one end can react with an amine on another end.

In some embodiments, exemplary functional groups on a flocculant include, but are not limited to: leavings groups, such as halides, including bromine and chlorine, tosylate, mesylate, and the like; or electrophilic groups, such as esters, including NHS esters, carbonates, and the like; or nucleophilic groups, such as amines, thiols, hydroxyl, and the like.

Purification and Selectivity

It has been discovered that the compositions and methods of the present disclosure are capable of separating a monomer and an aggregate to a greater degree and purity than previously known commercial separation products and methods. In some embodiments, the separation of a target molecule from impurities, including the separation of monomers from aggregates, in particular of a mAb from antibody/impurity aggregates, can be measured by the separation factor ($\alpha$) explained below.

$$\alpha = \frac{K_p^{Aggregate}}{K_p^{Monomer}} = \frac{\left(\frac{C_{Bound\,Aggregate}}{C_{Unbound\,Aggregate}}\right)}{\left(\frac{C_{Bound\,Monomer}}{C_{Unbound\,Monomer}}\right)} \quad (1)$$

$$K_p^{Aggregate} = \frac{C_{Bound\,Aggregate}}{C_{Solution\,Aggregate}} = \frac{\text{Aggregate Static Capacity}}{FT\ \text{Concentration} * \text{Total Aggregate \%}} \quad (2)$$

$$K_p^{Monomer} = \frac{C_{Bound\,Monomer}}{C_{Solution\,Monomer}} = \frac{\text{Monomer Static Capacity}}{FT\ \text{Concentration} * \text{Total Monomer \%}} \quad (3)$$

The separation factor can be used to determine if a particular molecule binds in high quantity or preference to a solid support as described herein, such as a bead or resin comprising a flocculant ligand covalently attached thereto, than does another molecule. In some embodiments, the separation factor can be used to determine if a monomer of an antibody binds in high quantity or preference to a solid support as described herein, such as a bead or resin comprising a flocculant ligand covalently attached thereto, than does an aggregate of the same antibody. Conversely, the separation factor can also be used to determine if an aggregate of an antibody binds in high quantity or preference to a solid support as described herein, such as a bead or resin comprising a flocculant ligand covalently attached thereto, than does a monomer of the same antibody. In some embodiments, the separation factor ($\alpha$) is greater than or equal to 1 indicating a preference for binding of aggregate compared to monomer. In some embodiments, the separation factor ($\alpha$) is greater than or equal to about 2. In some embodiments, the separation factor ($\alpha$) is greater than or equal to about 2.5. In some embodiments, the separation factor ($\alpha$) is greater than or equal to about 3. In some embodiments, the separation factor ($\alpha$) is greater than or equal to about 4. In some embodiments, the separation factor ($\alpha$) is greater than or equal to about 5. In some embodiments, the separation factor ($\alpha$) is greater than or equal to about 6. In some embodiments, the separation factor ($\alpha$) is greater than or equal to about 7. In some embodiments, the separation factor ($\alpha$) is greater than or equal to about 8. In some embodiments, the separation factor ($\alpha$) is in the range of about 2.5 to about 11. In some embodiments, the separation factor ($\alpha$) is in the range of about 4 to about 9.

In some embodiments, the separation factor ($\alpha$) is less than or equal to 1 indicating a preference for binding of monomer compared to aggregate. In some embodiments, the separation factor ($\alpha$) is from about 0.1 to about 1. In some embodiments, the separation factor ($\alpha$) is from about 0.1 to about 0.3. In some embodiments, the separation factor ($\alpha$) is from about 0.3 to about 0.6. In some embodiments, the separation factor ($\alpha$) is from about 0.6 to about 0.9.

The flocculant modified solid support may be utilized in several modes, including but not limited to bind and elute and flow through applications. Bind and elute applications can be applied when the target molecule and potentially its impurities bind to the solid support and are differentially separated by the action of an elution buffer. In the bind and elute mode of operation it is also possible that the impurities do not bind, or are not as strongly bound as the target molecule and are removed from the solid support by a flowing a wash buffer over the solid support. In some embodiments, a bind and elute mode of operation can provide a separation factor ($\alpha$) of less than or equal to 1, indicating a preference for binding of monomer compared to aggregate. For example, in a bind and elute mode of operation, when purification of a mAb is desired, and one of the contaminants is an aggregate of the mAb, then a separation factor ($\alpha$) of less than or equal to 1 will indicate that the mAb is bound to a separation medium of the present disclosure, while the aggregate of the mAb is removed from the solid support by a flowing a wash buffer over the solid support.

In the flow through mode operating conditions promote binding of impurities as the target molecule flow through the solid support to effect purification of the target molecule. In some embodiments, a bind and elute mode of operation can provide a separation factor ($\alpha$) of greater than or equal to 1, indicating a preference for binding of aggregate compared to monomer. In some embodiments, the separation factor ($\alpha$) in a flow through mode of operation is greater than or equal to about 2. In some embodiments, the separation factor ($\alpha$) in a flow through mode of operation is greater than or equal to about 2.5. In some embodiments, the separation factor ($\alpha$) in a flow through mode of operation is greater than or equal to about 3. In some embodiments, the separation factor ($\alpha$) in a flow through mode of operation is greater than or equal to about 4. In some embodiments, the separation factor ($\alpha$) in a flow through mode of operation is greater than or equal to about 5. In some embodiments, the separation factor ($\alpha$) in a flow through mode of operation is greater than or equal to about 6. In some embodiments, the separation factor ($\alpha$) in a flow through mode of operation is greater than or equal to about 7. In some embodiments, the separation factor ($\alpha$) in a flow through mode of operation is greater than or equal to about 8. In some embodiments, the separation factor ($\alpha$) in a flow through mode of operation is in the range of about 2.5 to about 11. In some embodiments, the separation factor ($\alpha$) in a flow through mode of operation is in the range of about 4 to about 9.

In some embodiments, recovery of target molecule can be up to 100%. In some embodiments, recovery of target molecule can be up to 99%. In some embodiments, recovery of target molecule can be up to 98%. In some embodiments, recovery of target molecule can be up to 95%. In some embodiments, recovery of target molecule can be up to 90%. In some embodiments, the purity of the recovered target molecule can be up to 100%. In some embodiments, the purity of the recovered target molecule can be up to 99%. In some embodiments, the purity of the recovered target molecule can be up to 98%. In some embodiments, the purity of the recovered target molecule can be up to 95%. In some embodiments, the purity of the recovered target molecule can be up to 90%.

Target Molecules or Molecules of Interest

Target molecules can be any biological molecule of interest, for example, monoclonal antibodies (including full length monoclonal antibodies), polyclonal antibodies, multispecific antibodies (e.g., bispecific antibodies), antibody fragments, immunoadhesins and antibody-immunoadhesin chimerias. An antibody may include, for example, an antibody of any molecule class, e.g., $IgG_1$, $IgG_2$, etc. that is to be purified from a mixture containing contaminants. An "antibody fragment" includes at least a portion of a full length antibody and typically, an antigen binding or variable region thereof; for e.g., they include Fab, Fab', F(ab')2, and Fv fragments; single-chain antibody molecules like camelid antibodies; diabodies; linear antibodies; and multispecific antibodies formed from engineered antibody fragments. The term "monoclonal" antibodies, indicates the character of the antibody as being obtained from a substantially homogeneous population of antibodies, and is not to be construed as requiring production of the antibody by any particular method. The monoclonal antibodies described herein include "chimeric" and "humanized" antibodies, and "human" antibodies, which can be isolated from various sources, including, e.g., from the blood of a human patient or recombinantly prepared using transgenic animals.

Exemplary target molecules may also include but are not limited to, proteins, enzymes, RNA, DNA, antibodies, cell parts, organelles, and the like. In some embodiments, the target molecule can be an enzyme, such as lysozyme, chymotrypsinogen, ribonuclease A, and the like. In some embodiments, the target molecule can be a protein, such as bovine serum albumin (BSA), cytochrome C, and the like. the target molecule is either a monomeric antibody, a therapeutic peptide or protein, a virus or viral particle, a particular variant of a peptide or protein or antibody or virus or viral particle, or a nucleic acid.

Chromatography

Solid supports that are built as chromatography resins, beads or particles can be used in column format, as is conventional practice, or in batch mode, such as in containers, bioreactors, bags, wells, flasks, etc., that are usually equipped with mechanisms for stirring. Solid supports such as membranes or filters would typically be manufactured for use in filter devices of which there are many designs.

In some embodiments it is likely that conditions can be identified to effectively inactivate viruses. These cases are highly desirable, as they eliminate the need for a viral inactivation hold and thus would be specifically amenable to continuous operations.

It will be appreciated that the separation media described herein will be exposed to certain conditions based on the desire application. In some embodiments, the separation medium is stable when contacted with an acidic or a basic solution, or at least one solvent. In some experiments, the at least one solvent can be any solvent known to one of skill in the art for use in chromatography applications. Suitable examples of solvents include, but are not limited to, aliphatic hydrocarbons, aromatic hydrocarbons, alcohols, ketones, aldehydes, glycol ethers, esters, glycol ether esters, and halogenic solvents. In some embodiments, the at least one solvent can be any common solvent, such as methanol, ethanol, acetone, ethylene glycol, acetonitrile, water, acidic solutions, basic solutions, and the like.

Various applications using the materials and methods described herein are envisioned, as would be clearly understood by one of skill in the art. These include, but are not limited to, high performance liquid chromatography (HPLC); solid phase extraction; purification from either a harvested cell culture fluid, a cell culture supernatant, or a conditioned cell culture supernatant, a cell lysate, or a clarified bulk; from wherein a target biomolecule or protein is purified; or, sample prep.

The first chromatography can be selected from an affinity chromatography, ion exchange chromatography, hydrophobic interaction chromatography, or mix-mode chromatography. The second chromatography can be ion exchange chromatography, hydrophobic interaction chromatography, a mix-mode chromatography. The second chromatography can be positive-charged membrane chromatography or hydrophobic interaction membrane chromatography.

In certain purification protocols, where the separation medium as described herein, such as a caprylic acid derivitized resin, is used in column chromatography, the load material may be a clarified or an unclarified feed, or a pool from an affinity purified step, an ion exchange step, from HIC purification, from mixed mode purification, from reverse phase column, or from any other chromatography step. The load material concentration may be any concentration that allows the molecule to be soluble at 0.1 mg/mL to >100 mg/mL. The pH of the load solution may be adjusted between about pH 1 and about pH 14 before loading on to the chromatographic column with a separation medium as described herein, such as a caprylic acid derivitized resin. The pH of the load solution may be adjusted between about pH 1 and about pH 7 before loading on to the chromatographic column with a separation medium as described herein, such as a caprylic acid derivitized resin. In certain purification protocols, the pH of the elution solution may be adjusted between about pH 3 and about 13, or between pH 3 and about pH 7 before the proceeding step, or, the solution may be adjusted before taking the solution to the next chromatographic step. In some purification protocols, the elution mixture may not be subjected to additional chromatography steps, and could be the final purification step.

Buffers

The buffer composition ranges can be protein dependent. For example, elution may be carried out using salt to displace monomer, or by pH change of at least 1 pH unit, or a combination thereof. Use of additives such as polymers, alcohols, or amino acids may be used to control the degree of secondary or tertiary interaction or a combination thereof. As described herein, in the flow-through mode, impurities are bound and the target molecule flows through with zero to minimal interaction with the resin. As described herein, in the bind and elute mode, both the impurity and the target molecule bind to the surface, and the target molecule or the impurity can be selectively eluted through a change in salt concentration, salt type, pH, through the use of additives. In an alternative embodiment, both the impurity and the target molecule bind, and the target molecule is then displaced by the impurity or by a competitive additive (displacer). In some embodiments, the materials and methods described herein can be applied to lab scale sample preparation (such as 10 μL to 50 mL bed volume). For use in semi preparative scale sample preparation (10 mL to 1 L bed volume). In some embodiments, the materials and methods described herein can be applied to large scale purification above 1 L bed volume.

In some embodiments, the separation medium is capable of separating a monomer and an aggregate of the same biological molecule in a pH range of about 2 to about 11. In some embodiments, the separation medium is capable of separating a monomer and an aggregate of the same biological molecule in a pH range of about 4 to about 8. In some embodiments, the separation medium is capable of separating a monomer and an aggregate of the same biological molecule in a pH range of about 5 to about 7. In some embodiments, the separation medium is capable of separating a monomer and an aggregate of the same biological molecule in a pH range of about 4.5 to about 7.5.

It will be appreciated that while the separation media and methods described herein can be operated in buffer systems over a wide range of pH, the separation media and methods described herein can be operated at a wide range of buffer conductivity. In some embodiments, the buffer conductivity can be 0 mS/cm to about 200 mS/cm. In some embodiments, the buffer conductivity can be about 0 mS/cm to about 30 mS/cm. In some embodiments, the buffer conductivity can be about 10 mS/cm to about 30 mS/cm. In some embodiments, the buffer conductivity can be about 1 mS/cm to about 20 mS/cm. In some embodiments, the buffer conductivity can be about 30 mS/cm to about 135 mS/cm. In some embodiments, the buffer conductivity can be about 30 mS/cm to about 75 mS/cm. In some embodiments, the buffer conductivity can be about 50 mS/cm to about 135 mS/cm. It will be further appreciate that the conductivity can be expressed in terms of buffer concentration. In particular, higher ion concentration, provides higher conductivity. Conversely, lower ion concentration, provides lower conductivity. The buffer for use in connection with the present disclosure is not particularly limited, and can be any buffer known in the art for use in separation or purification of biological molecules. For example, in some embodiment, the buffer can be aqueous NaCl in a concentration of about 5 mM to about 2M. In some embodiments, the buffer can be aqueous NaCl in a concentration of about 5 mM to about 1M, 5 mM to about 500 mM, 5 mM to about 300 mM. In some embodiment, the buffer can be aqueous NaCl in a concentration of about 5 mM, about 25 mM, about 75 mM, about 100 mM, about 200 mM, about 300 mM, about 500 mM, about 1M, about 1.5 M, about 2M.

EXAMPLES

Bioprocessing chromatography resins are ubiquitous in the manufacture of biotherapeutics and are essential for the removal of product and process related impurities. In this segment once resins are selected, they are qualified and processed and filed with the FDA. With increasing numbers of new molecule modalities, resins with differentiated resin functionalities are needed. We have created novel resins with unique surface chemistries (flocculant ligands) and generated a new line of flocculant ligand functionalized purification resins that clearly distinguish from any of the existing commercial purification products available.

Example 1: Exemplary Cationic Exchange (CEX) Flocculant Resins

Precipitation or flocculation of protein A-purified-antibody using caprylic acid (CA) or octanoic acid, in solution, is currently known, and the CA precipitation method is exemplified in Biotechnology and Bioengineering, Vol. 109, No. 10, 2012, 2589-2598). However, no attempts have been made so far to immobilize caprylic acid or any other flocculant on to resins to generate purification resins, or to use immobilized flocculant resins for protein purification.

To generate a cationic exchange flocculant surface, typically, any anionic ligands, such as an unsubstituted or substituted aliphatic carboxylic acid, an unsubstituted or substituted aromatic carboxylic acid, an unsubstituted or substituted aliphatic sulfonic acid, an unsubstituted or substituted aliphatic acrylic acid, an unsubstituted or substituted aliphatic thiosulfate, an unsubstituted or substituted aliphatic phosphonic acid, or an unsubstituted or substituted aliphatic phosphoric a fatty acid, may be used as a ligand to couple to any base surface. Typically, the unsubstituted or substituted aliphatic groups are either linear or branched, and optionally, comprise one or more double bonds. Furthermore, the unsubstituted or substituted aliphatic groups can have from 1 to about 30 carbon atoms, preferably from 1 to about 20 carbon atoms, more preferably from about 1 to about 10 carbon atoms, most preferably from about 1 to about 8 carbon atoms.

In an exemplary embodiment demonstrated here, cationic exchange flocculant resins were generated by coupling anionic flocculants such as unsubstituted or substituted $C_1$-$C_8$ aliphatic acids to base surfaces. In one exemplary embodiment, the CEX flocculant resin comprised caprylic acid.

In the exemplified embodiment shown here, the base surface is a resin or a bead. However, one of skill in the art would recognize that the base surface can include and not be limited to: a resin, bead, sphere, particle, microcarrier, membrane, web, bag, bioreactor, tube, plate, array, flat surface, filter, fiber or a fabric.

It has been discovered that the compositions and methods using CEX flocculant resins are capable of separating a monomer and an aggregate to a greater degree and purity than previously known commercial separation products and methods. In some embodiments, the separation of a target molecule from impurities, including the separation of monomers from aggregates, in particular of a mAb from antibody/impurity aggregates, can be measured by the separation factor ($\alpha$) explained below.

Typically, during purification, antibody input samples (feeds) after protein A column purification still contain impurities like high molecular weight (HMW) and low molecular weight (LMW) species as shown in FIG. 1a. The aggregate species peaks are labeled as HMW/LMW 1, 2, 3, and they need to be separated from the monomer. HMW impurities can include aggregates (dimers, trimers, tetramer etc, and/or, antibody monomer with a light chain, and/or antibody with high levels of post translational modifications, and/or aggregated host cell proteins (HCP), and/or aggregated antibody or protein fragments. LMW impurities can include host cell proteins (HCP) or antibody or protein fragments. It was surprisingly observed that, the novel surface functionalities (flocculant ligands resins as shown in exemplary Resins A, B, C and D) dramatically improve the removal of high molecular weight and low molecular weight species (including antibody aggregates) by selectively binding to the aggregates over the monomers under certain selectivity conditions. see FIGS. 1b, 1c, 1d and 1e.

Resin preparation: Exemplary flocculant resins were prepared as follows. The flocculant caprylic acid (octanoic acid) was immobilized on to a POROS chromatography resin for evaluation of intended use for purification of biomolecules. In a specific embodiment, this example describes immobilization of bromo-caprylic acid to the POROS resin by activation of surface hydroxyl groups and an $S_N2$ substitution reaction. The resin could have equally been prepared by coupling hydroxy-caprylic acid/or its derivative to an expoxide activated POROS resin. The POROS resin had a pore mode of ~1,000 Å, and was manufactured and coated with a polymeric coating containing a high density of hydroxyl groups. Approximately 2 g of the POROS beads was contacted with a solvent (~12 mL of dioxane, dimethylformamide or dimethyl sulfoxide) containing ~1.5 to 2.0 g of 8-bromo-caprylic acid and tertiary butoxide (~0.75 M). Bromo-caprylic acid was immobilized by heating the reaction mixture to ~60° C. in about 1 hour and holding the reaction mixture at this temperature for between 4 to 96 hours. At the end of the hold time, the resin was filtered to remove the reaction solution, and was washed with methanol (7×10 mL), then with water (2×10 mL), to remove the organic base and the unreacted bromo-caprylic acid. Subsequently the resin was transferred into a solution containing 1 M sodium hydroxide for storage before use.

Resin evaluation: Evaluation of the resin comprised measurement of the ionic capacity of the resin as a measure of the surface density of the caprylic acid. This was determined by packing of a chromatography column, treating the resin in the column with a dilute acid solution to ensure the hydrogen form of the surface and titration with a dilute solution of sodium hydroxide. Assessment of the volume of sodium hydroxide needed to achieve 50% breakthrough as noted by a pH meter determines the ionic capacity of the resin. In this example the ion capacity was ~64 μmol/mL.

High throughput screening was used to determine static binding capacity and to map potential operating parameters that could be useful for purification of a therapeutic molecule such as a monoclonal antibody (mAb). Here, we looked at the ability of the resin to selectively bind to the aggregate over the antibody monomer. The equilibrium binding capacity of a mAb was assessed by contacting the mAb in an appropriate buffer solution with the resin that had been conditioned with the same solution, incubating the resin/mAb combination with gentle agitation, and after an incubation time of ~1 hour, recovering the supernatant solution for measurement by UV at a wavelength of 280 nm. The absorbance of this filtrate was compared with the absorbance of the initial mAb solution to determine the amount of the mAb that bound to the caprylic acid functionalized resin. Results are shown in TABLE 1 below.

ined in this test. As noted by relative high alpha values, it was predicted that Resin A/or other derivative flocculant resins had higher selectivity for aggregates under certain operating conditions than commercially available weak carboxy methyl cation exchangers (competitor 1 CM and competitor 2 CM) and a commercially available strong cation exchanger (POROS XS) used under the same conditions (also see Tables 2 and 3 below, which show high a values or higher selectivity for aggregates at given pH and salt concentration). This exciting finding was further examined by purification experiment of the same mAb. Under static binding conditions, we are looking at the ratio of bound and unbound monomer and aggregate. The higher alpha, the more aggregate was bound in comparison to the monomer. As seen in Tables 2 and 3, purification resin type A showed significant increase in selectivity for aggregates compared to POROS XS and competitor resin over a wide range of conditions. Under certain conditions, resin type A bound almost the same amount of aggregates as POROS XS resin, while only binding approximately one quarter of the monomer. Thus, resin type A was a great candidate for flow through chromatography to purify monomer, possibly even overload chromatography.

In the next study, a slurry of caprylic acid flocculant resin A in aqueous 0.1M sodium chloride was packed into a 4.6 mm×10 cm stainless steel column at a pressure of 100 bar. The column was then conditioned with 5 to 10 column volumes at a flow rate of 150 cm/hr with a buffer comprising 20 mM MES buffer at pH 5.5 to which 1 M sodium chloride was added. A monoclonal antibody (mAb) solution with 5% aggregate was loaded on a Resin A column under flow-through conditions (high salt) (see FIG. 1b). The feed solution containing the target mAb and an amount of a form

TABLE 1

Static Binding Capacity (mg mAb/mL resin)

| | Resin Type A | | | Competitor 1 CM | | | Competitor 2 CM | | | POROS XS | | |
|---|---|---|---|---|---|---|---|---|---|---|---|---|
| | 5 mM NaCl | 25 mM NaCl | 75 mM NaCl | 5 mM NaCl | 25 mM NaCl | 75 mM NaCl | 5 mM NaCl | 25 mM NaCl | 75 mM NaCl | 5 mM NaCl | 25 mM NaCl | 75 mM NaCl |
| pH 4.5 | 23.1 | 22.1 | 23.4 | 80.0 | 81.9 | 85.0 | 74.3 | 78.6 | 64.9 | 82.6 | 92.3 | 96.1 |
| pH 5.5 | 27.1 | 28.4 | 26.2 | 91.9 | 97.0 | 62.7 | 83.1 | 78.0 | 25.9 | 99.6 | 102.5 | 80.5 |
| pH 6.5 | 32.8 | 22.8 | 17.2 | 84.7 | 97.1 | 37.8 | 42.4 | 47.1 | 19.9 | 90.5 | 97.7 | 56.6 |
| pH 7.5 | 31.8 | 21.2 | 9.3 | 97.4 | 82.4 | 7.3 | 53.7 | 38.9 | 6.9 | 100.0 | 88.0 | 12.7 |

The data from the CEX flocculant resin was compared to that of commercially available weak (carboxy methyl) cation exchangers (competitor 1 CM and competitor 2 CM), and a commercially available strong cation exchanger (POROS XS). There is a predictable wider operating range than is observed for the commercially available resins. Comparison of the Static Binding Capacity (SBC) for different resins at representative pH and salt concentrations. Table 1 shows data for Resin A; data for Competitor 1 resin; data for Competitor 2 resin; data for POROS XS. In addition to the conditions represented in the table herein, pH can be varied over a range of pH 2.0-9.0, and the salt concentrations can be varied from 0.0 M to 1.5 M salt in order to achieve a desirable SBC.

Figure 1B:
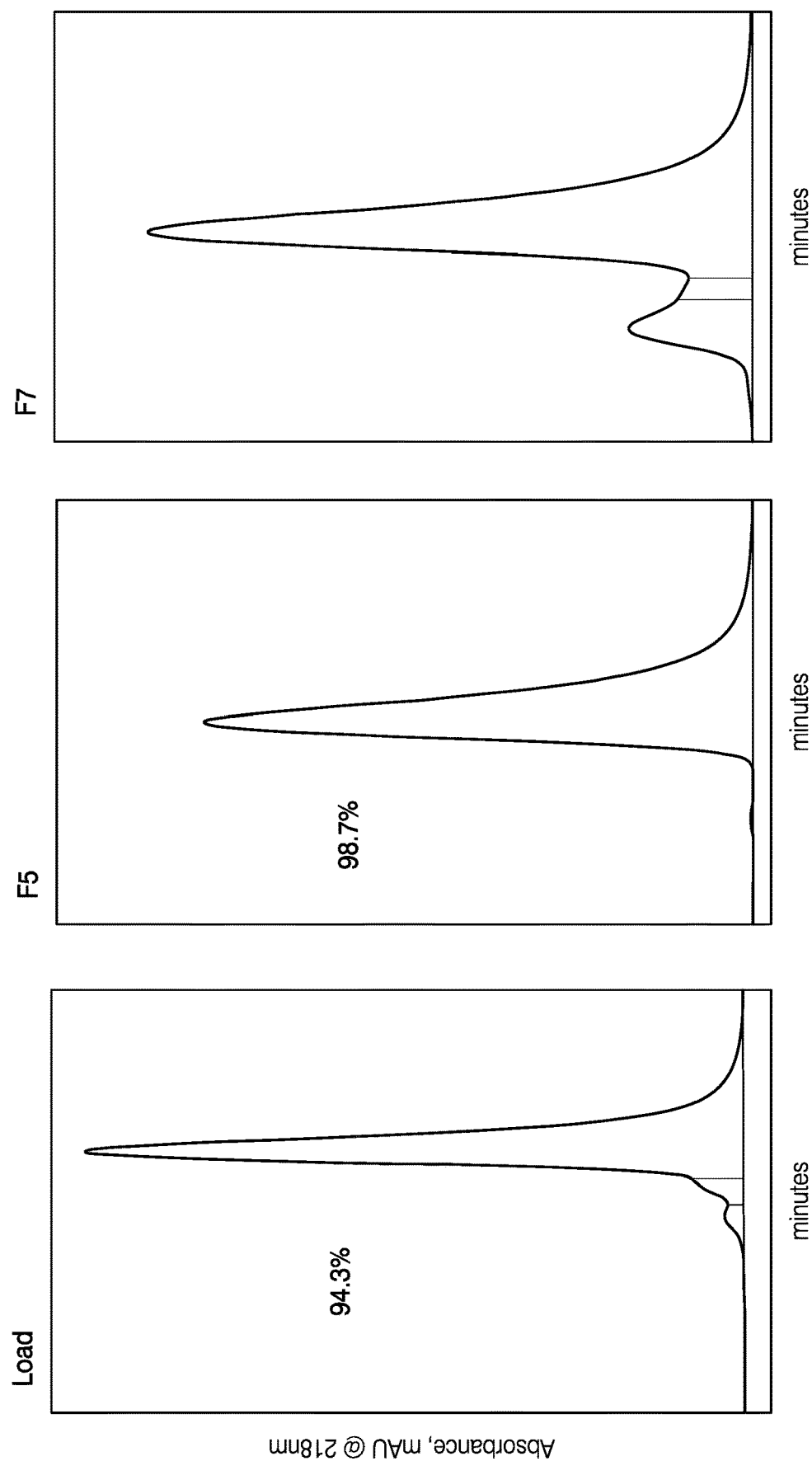
FIG. 1b: demonstrates the effective removal of aggregate species, including the removal of closely related dimer impurity in a purification run with Flocculant Resin A. The panels demonstrate the effectiveness of aggregate removal in F5 (fraction 5) compared to the load, and the subsequent breakthrough fraction (F7). The feed (Load) is already 94.3% pure but contains HMW and LMW species. Resin A effectively removes closely related, difficult to purify HMW spps (monomer plus additional light chain). The HMW and LMW aggregate species seem to bind selectively to Resin A while the monomer flows through (monomer flow-through=98.7% purity). Exemplary resin A was able to remove close to 100% of the higher molecular weight species.
Figure 1C:
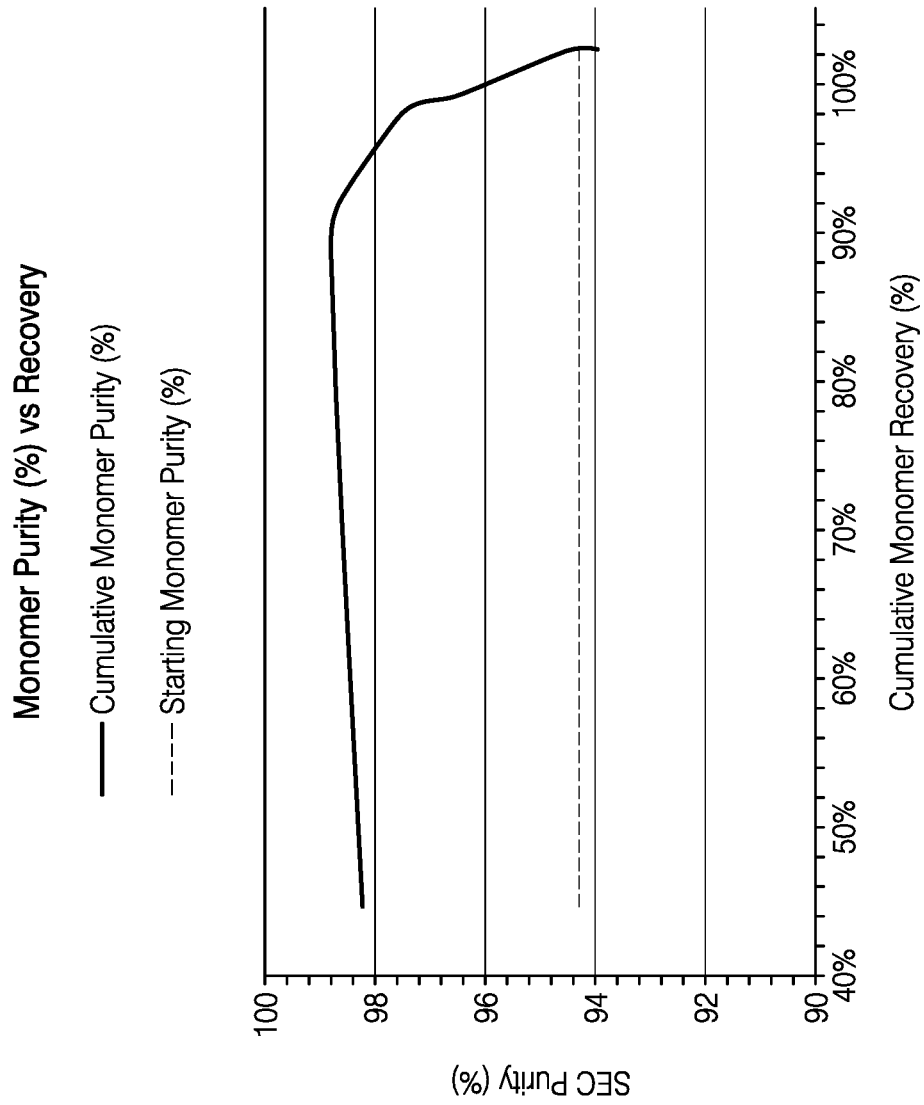
FIG. 1c: The graph shows the yield—the cumulative monomer recovery (%) vs. the purity (%) of the monomer when purified on Resin A (as discussed in FIG. 1b above). The sample purity falls gradually after fraction 5 (which alone, shows 90% recovery).

The data predicts a wide operational space for the removal of aggregate from the mAb (monoclonal antibody) examof the mAb with an extra light chain, (first panel, Load, FIG. 1b) in same equilibration buffer, was contacted with the resin at a flow rate of 150 cm/hr until the equivalence of 10 g of mAb per liter of resin, and was passed through the column. Upon completion of the load of the mAb a gradient to 0% sodium chloride over 20 CV was applied to the column to elute bound proteins. Fractions were collected throughout the flow through and elution period of this purification example. Each fraction was analyzed by size exclusion chromatography to determine composition. Second panel (F5) and third panel (F7) of FIG. 1b shows the purity of fractions 5 and 7, respectively. The protein with the extra light chain was completely removed in the first 5 to 6 fractions of this experiment, thus demonstrating significant power of novel resin A for removal of a closely related product impurity. It was noted that the first 6 fractions consisted of monomer with a purity of >98% (see graph, FIG. 1c). In the graph of FIG. 1c, Monomer vs Recovery, shows the Cumulative Monomer Recovery (%) vs. Purity (%) when purified on Resin A. The sample purity falls gradually after fraction 5 as the impurity begins to elute with the remaining monomer (which alone, shows 90% recovery).

Figure 1D:
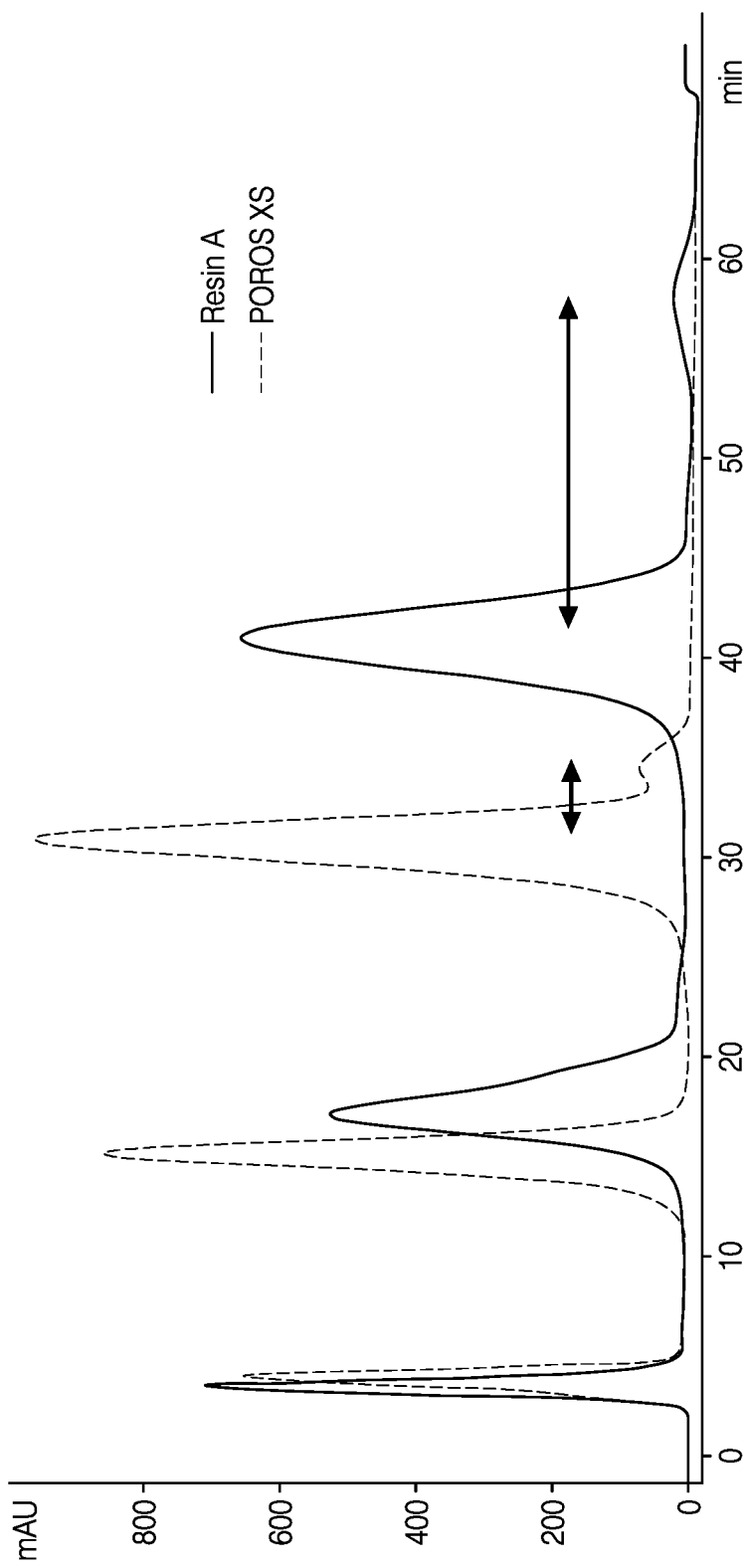
FIG. 1d: shows the purification of three sample proteins myoglobin (Protein 1), alpha-chymotrypsinogen A (Protein 2), and lysozyme (Protein 3), on Resin A. Resin A has greater selectivity for the impurity compared to a control, non-flocculant, cation exchange (CEX) resin POROS XS—compare the separation of the impurity peak from the monomer between the two resins, as pointed out by the bold arrow. This suggests that Resin A is a better choice for the removal of impurities than standard ion exchange purification.
Figure 1E:
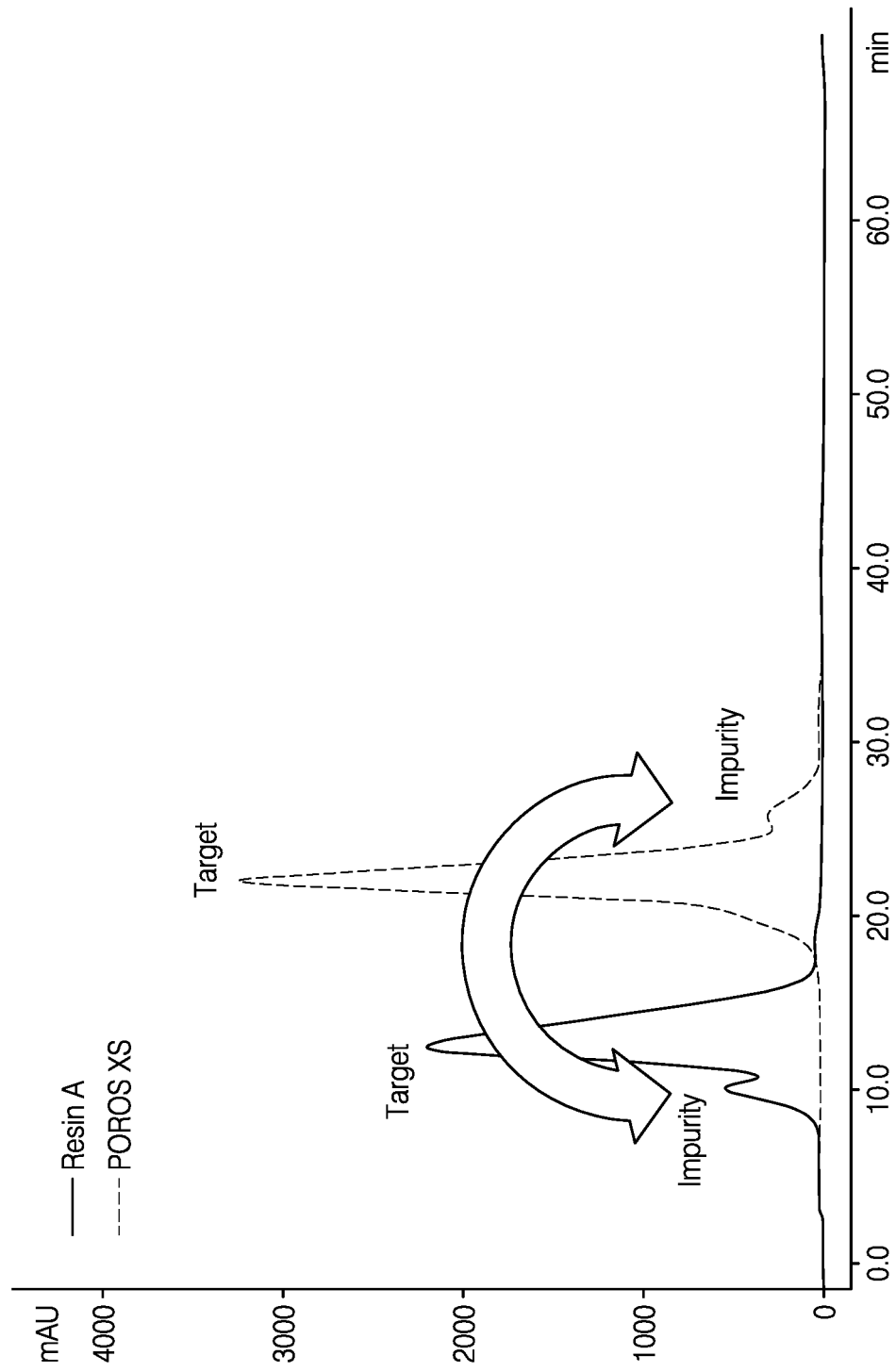
FIG. 1e: shows the separation of two very similar proteins on Resin A compared to control, non-flocculant, cation exchange (CEX) resin POROS XS. Here, the impurity protein=cytochrome C and the target protein=ribonuclease A. Resin A has an alternative selectivity profile compared to that POROS XS resin.

To determine the effectiveness across different types of protein molecules and to confirm whether selectivity is different from POROS XS, we looked at a low mass load of standard proteins with different molecular weight (mwt), isoelectric point pI and hydrophobicity. Protein retention is surface dependent shown through different retention time on each flocculant resin type compared to POROS XS, when exposed to the same analysis conditions. In FIGS. 1d and 1e, we took very similar proteins and applied them to Resin A and benchmark resin POROS XS.

FIG. 1d, Conditions: Column dimensions: 4.6 mm×100 mm; Total protein load ~1.2 mg; Sample proteins studied were: ~0.2 mg Myoglobin (Protein 1, mwt 16.9 kDa, pI 7.36); ~0.5 mg Alpha-Chymotrypsinogen A (Protein 2, mwt 25.6 kDa, pI 8.52); ~0.5 mg Lysozyme (Protein 3 mwt 14.4 kDa, pI 11.35). Separation based on size exclusion would be indicated by elution in order of molecular weight or size (cytochrome c<lysozyme<chymotrypsinogen). Separation based on hydrophobicity would be in the order: Cytochrome c<lysozyme<chymotrypsinogen. For POROS XS, the expected elution order is based on pI through ion exchange: Chymotrypsinogen<cytochrome c<Lysozyme, with minimal effects based on size or hydrophobicity. In the graph on FIG. 1d, it is clear that Resin A has a greater selectivity for the more hydrophobic protein, lysozyme and its impurities (see arrow or separation in impurity peak) suggesting that Resin A is a better choice for the removal of impurities than standard SCX purification.

To study the efficiency of separation of an impurity from target, purification of two similar proteins were studied on Resin A (see FIG. 1e). The conditions were: Column dimensions: 4.6×100 mm (CV=1.66 mL) Gradient 0.1-0M NaCl in 4 min. Total Protein Load=9.3 mg.
The impurity protein=Cytochrome C; protein amount=4.1 mg; MW=12.3 kDa; pI=10.3;
TARGET protein=Ribonuclease A; protein amount=5.2 mg; MW=13.7 kDa; pI=9.6.
From the graph in FIG. 1e, it is clear that novel Resin A has an alternative selectivity profile compared to that of the control POROS XS resin. Here, a steep gradient was used in the purification; however, it's clear that you can choose load conditions that would allow target or impurity to bind or flow through as desired, to get a selectivity switch.

Example 2: Selectivity Evaluations of Cation Exchange (CEX) Flocculant Resins A, B, C, D In exemplary embodiments, aliphatic flocculant chains of varying lengths were conjugated to porous resins. The resins differed in their hydrophobicities as follows: A>>>B>>C>D, where A is comparatively the most hydrophobic, compared to B and C with intermediate hydrophobicity, compared to prototype D with the least hydrophobicity. Resins A, B and D were prepared using the same methods described in Example 1, whereas Resin C was prepared using a slight variation of Example 1.

Further evaluation of the operational space of cation exchange flocculant resins was done by a determination of the selectivity factor α of the flocculant resins A-D for monomer versus impurities or high and low molecular weight aggregate forms of the mAb. In this experiment the resin was eluted with a suitable buffer to recover proteins that bound to the resin. Both filtrate and eluate were analyzed by size exclusion chromatography to determine concentrations of bound and unbound monomer and aggregate. This information was used to determine an alpha factor (as noted in equation 1), which under the operating conditions described above, is a measure of the selectivity of the flocculant resins for aggregates compared to monomer.

$$\alpha = \frac{K_p^{Aggregate}}{K_p^{Monomer}} = \frac{\left(\frac{c_{BoundAggregate}}{c_{UnboundAggregate}}\right)}{\left(\frac{c_{BoundMonomer}}{c_{UnboundMonomer}}\right)}$$ Equation 1

Separation/Selectivity Factor (α)>1

We screened selectivity of flocculant resins Resins A, B, C and D by looking at the selective removal of aggregated species from a Protein A purified antibody solution. We also benchmarked their selectivity/separation factors (α) against commercial, non-flocculant, cation exchange resins like POROS XS, X-CM and Y-CM (See Tables 2-3). The separation factor can be used to determine if a particular molecule will bind in high quantity or preference to a solid support or base surface as described, such as a bead or resin or membrane comprising a flocculant ligand covalently attached thereto, than does another molecule. The numbers highlighted in bold in Tables 2-3 indicate preferred high selectivity/separation factors, whereas the numbers not highlighted indicate less-desirable, low selectivity/separation factors.

In a certain embodiment, the separation factor (α) is greater than 1, indicating a preference for binding of aggregate compared to monomer. The separation factor can be used to determine if a monomer of an antibody binds in high quantity or preference to a solid support as described herein, such as a bead or resin comprising a flocculant ligand covalently attached thereto, than does an aggregate. In TABLES 2 and 3, selectivity factors higher than 2.0 and 4.5 respectively are shown in bold, which show conditions where aggregates including very closely related HMW species, bind preferentially to the flocculant resin columns. This region has high selectivity for aggregates. In this embodiment, the pure monomer is not expected to bind to the resin and thus the monomer can be collected in flow through mode. If we compare the selectivity factors of Tables 2-3 across the control resins and the flocculant resins A-D, we see that the operational window with high selectivity is greater for the flocculant resins than the commercial, non-flocculant resins.

In some embodiments, the separation factor (α) is greater than or equal to about 2. In some embodiments, the separation factor (α) is greater than or equal to about 2.5. In some embodiments, the separation factor (α) is greater than or equal to about 3. In some embodiments, the separation factor (α) is greater than or equal to about 4. In some embodiments, the separation factor (α) is greater than or equal to about 5. In some embodiments, the separation factor (α) is greater than or equal to about 6. In some embodiments, the separation factor (α) is greater than or equal to about 7. In some embodiments, the separation factor (α) is greater than or equal to about 8. In some embodiments, the separation factor (α) is in the range of about 2.5 to about 11. In some embodiments, the separation factor (α) is in the range of about 4 to about 9.

In addition to the conditions represented in the tables herein, pH can be varied over a range of pH 2.0-11.0, preferably over a range of pH 2.0-9.0 under normal use conditions; the salt can be varied from concentrations of 0.0 M to 1.5 M salt in order to achieve a desirable separation factors. Kp is the partition coefficient for either the aggregate or the monomer.

Figure 2A:
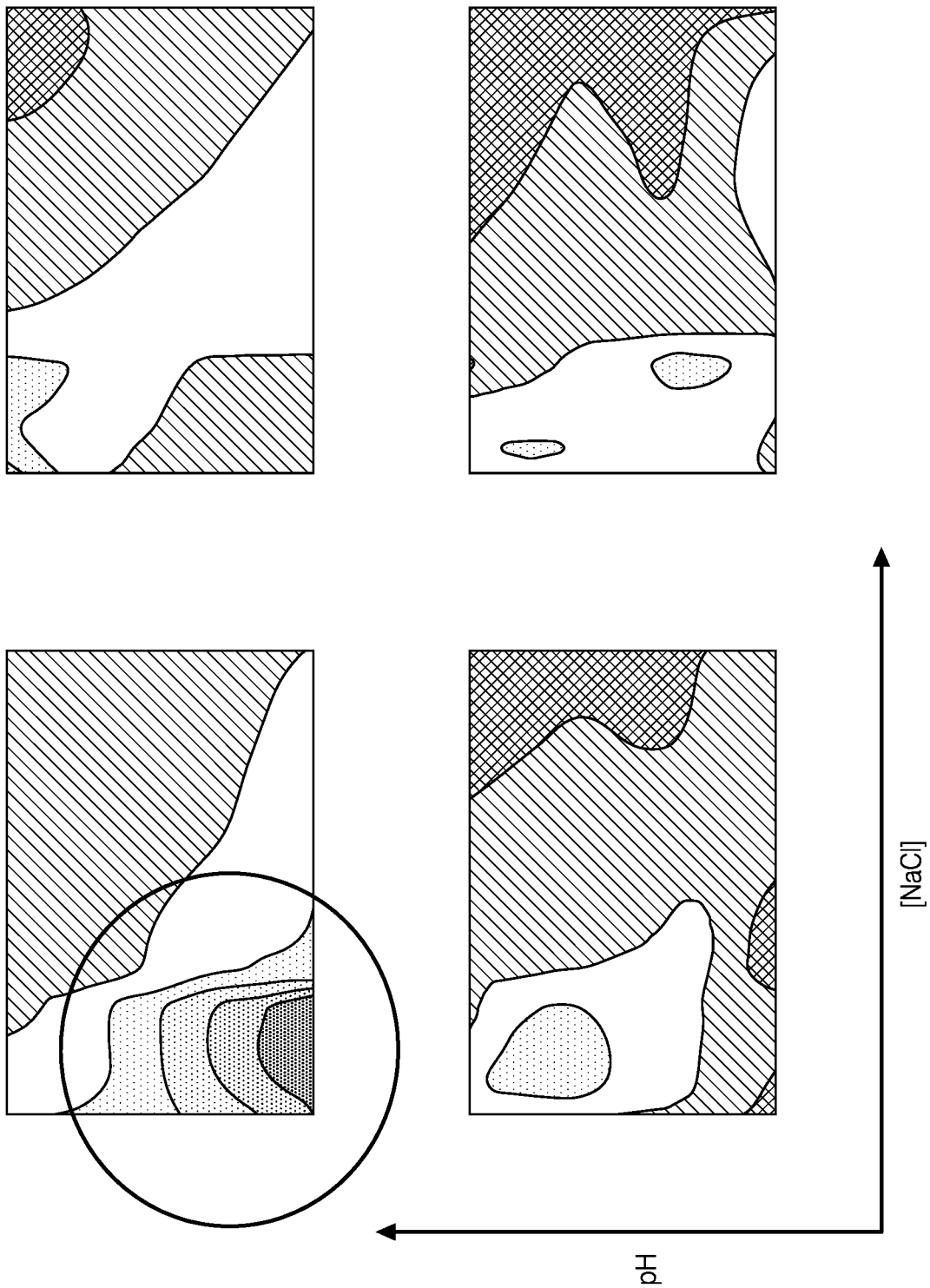
FIG. 2a: Heat Map showing the selectivity factor ($\alpha$) for the following resins: Top left panel=Resin A compared to commercial products (non-flocculant, cation exchange (CEX) resin controls): Top right panel=POROS XS (control, non-flocculant ligand resin); Bottom left panel=CEX-CM (control, non-flocculant ligand resin); Bottom right panel=CEX-YM (control, non-flocculant ligand resin). The heat map shows that resin A had the best selectivity for the removal of aggregated species from a Protein A purified antibody solution compared to control resins (see region with dark dots).
Figure 2B:
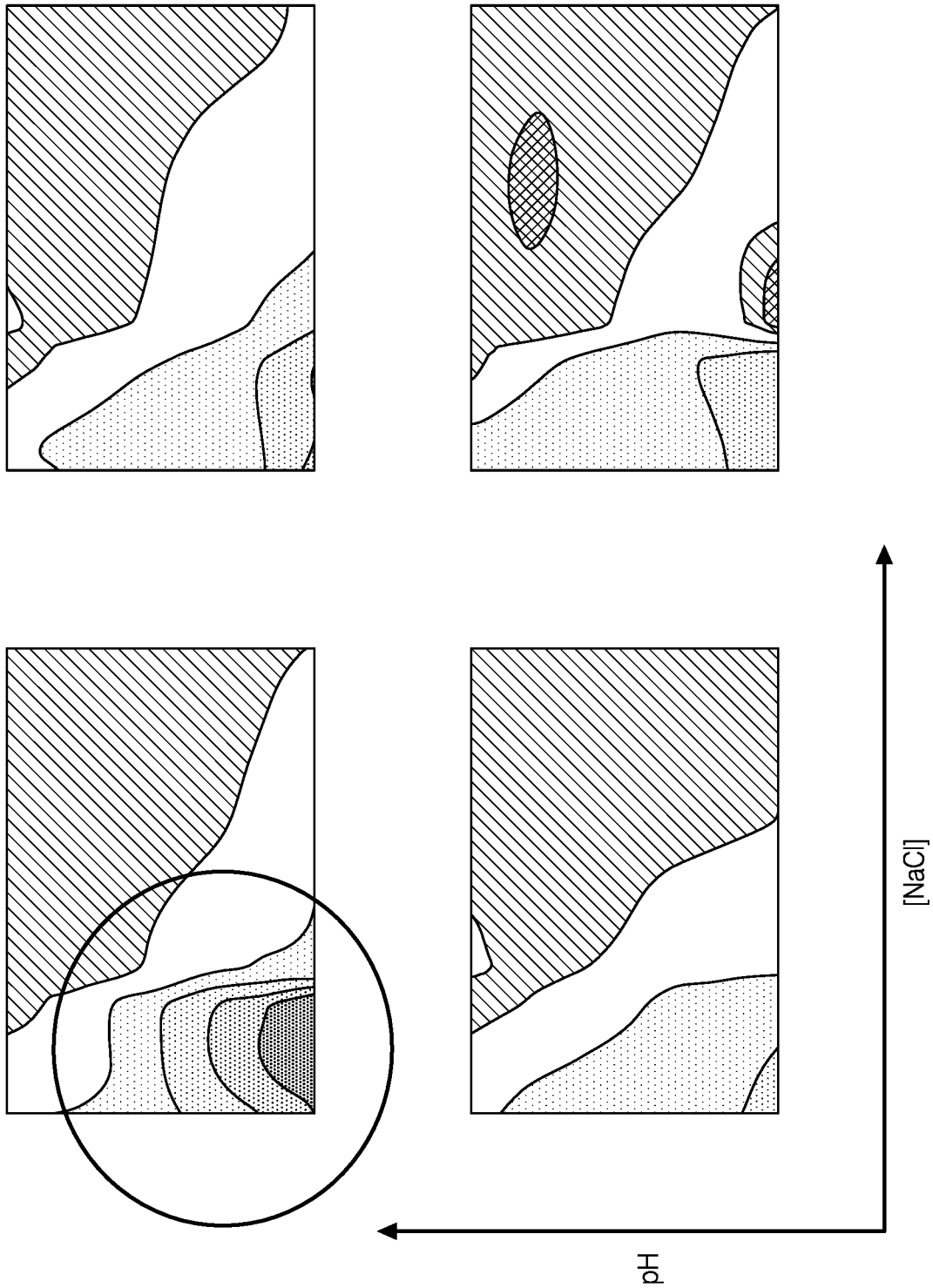
FIG. 2b: Heat Map showing the effects of pH and salt concentration on the selectivity factor ($\alpha$) ranges for the following exemplary flocculant-ligand resins of the present disclosure: Top left panel=Resin A; Top right panel=Resin B; Bottom left panel=Resin C; Bottom right panel=Resin D. The heat map show that all exemplary resins A, B, C and D showed good selectivity for the removal of aggregated species from a Protein A purified antibody solution. The heat map is based on selectivity factor ($\alpha$) data shown in TABLES 2 and 3. If we compare the heat map across the control resins of 2a and the flocculant resins A-D, we see that the operational window with high selectivity is greater for the flocculant resins than the commercial, non-flocculant resins.

We also provide contour heat maps in FIGS. 2a and 2b based on the selectivity data from the Tables 2-3. The heat maps show the effect of pH and salt concentration on the selectivity factors α for a given resin. The darker the dots on the contour plot=the HIGHER the value of the separation factor (α), which show conditions where aggregates bind preferentially to the flocculant resin. Regions on the plot with relatively higher density of dark dots showing the best selectivity/separation for aggregate (which binds the resin in this case) than for monomer, in a given mode of operation. Regions with relatively lighter density of dots and lighter shade of dots show operational ranges with slightly less selectivity of aggregate over monomer under the operating conditions.

FIG. 2a shows a heat map comparison of the exemplary separation medium Resin A versus non-flocculant, control resins POROS XS, X-CM and Y-CM. If we take a look at the heat map across the benchmark, non-flocculant resins, the operational window with high selectivity is greater for the flocculant resins than for the commercial, non-flocculant resins.

FIG. 2b shows a heat map comparison of an exemplary separation media—Resins A, B, C and D with each other. The resins show a range of ligand hydrophobicities: Resin A>>>B>>C>D, which A being the most hydrophobic resin. All resins A-D display increased selectivity for aggregates with selectivity factors>>1, over a broad range of pH and salt concentrations. Thus, the flocculant-ligand resins showed greater aggregate selectivity across a range of hydrophobicities, across broader modes of operation (pH and salt concentration). Exemplary salt ranges studied were in the range of 0-3 M Salt; pH range=1-12; the optimum range will be protein dependent.

Separation/Selectivity Factor (α)<1

Conversely, by changing the mode of operation (for e.g., salt concentration, salt type, pH, buffer type, addition or absence of solutes, conductivity, etc.) the separation factor values can be shifted such that the aggregate does not bind to the resin, but instead, the monomer binds to the separation medium in high quantity. In other words, the monomer shows preference for the solid support with flocculant. In some embodiments, the separation factor (α) is less than 1. In some embodiments, the separation factor (α) is from about 0.1 to about 0.9. In some embodiments, the separation factor (α) is from about 0.1 to about 0.3. In some embodiments, the separation factor (α) is from about 0.3 to about 0.6. In some embodiments, the separation factor (α) is from about 0.6 to about 0.9.

In TABLE 4, selectivity factors of lesser than 0.9 are shown in bold, which are conditions where monomers bind preferentially to the flocculant base surfaces, resins or columns than any aggregate or any other HMW/LMW species. In such conditions, the monomer may be purified in bind-elute mode.

In some embodiments, the separation factor (α) is 1, which means that neither the monomer nor the aggregate species can be separated effectively. Therefore, for selectivity or separation of monomer from aggregate, or ligate from solution, or target molecule from impurity, the operating conditions must be manipulated such that the selectivity factor is either >1 (when aggregate/impurity binds, thus monomer/target can be purified in flow-through mode), or the selectivity factor is <1 (when the monomer/target binds, thus the monomer/target can be purified in bind-elute mode). One of skill in the purification art would know to manipulate such modes of operation and to fine tune purification conditions in order to achieve the binding/separation of a desired target.

In addition to the conditions represented in the tables herein, pH can be varied over a range of pH 2.0-9.0; the salt can be varied from concentrations of 0.0 M to 1.5 M salt in order to achieve a desirable separation factors. $K_p$ is the partition coefficient for either the aggregate or the monomer.

TABLE 2

Selectivity Factor (α) for Cationic Flocculant Resins Types A-D and benchmark resins;
Bold numerals when (α) > 2.5 = good selectivity for aggregate species (HMW); Monomer purified in flow-through mode.

| pH | 4.5 | | | | | | 5.5 | | | | | | 6.5 | | | | | |
| --- | --- | --- | --- | --- | --- | --- | --- | --- | --- | --- | --- | --- | --- | --- | --- | --- | --- | --- |
| mM NaCl | 5 | 25 | 75 | 100 | 200 | 300 | 5 | 25 | 75 | 100 | 200 | 300 | 5 | 25 | 75 | 100 | 200 | 300 |
| POROS XS | 1.05 | 1.39 | 1.73 | 3.67 | 3.1 | 1.75 | 1.71 | 1.21 | 1.7 | 3.86 | 1.99 | 1.26 | 1.96 | 2.45 | 3.51 | 2.62 | 1.35 | 1.06 |
| Competitor X | 0.68 | 0.9 | 1.4 | 0 | 1.91 | 1.27 | 1.57 | 2.34 | 2.27 | 2.28 | 1.2 | 0.94 | 2.11 | 4.77 | 4.04 | 1.94 | 1.17 | 0.94 |
| Competitor Y | 1.93 | 1.82 | 2.48 | 1.81 | 3.35 | 0.89 | 2.6 | 2.91 | 4.39 | 1.4 | 0.98 | 0.84 | 3.44 | 3.9 | 2.19 | 1.65 | 1.13 | 0.92 |
| Resin Type A | 9.73 | 11.4 | 11.77 | 4.29 | 3.73 | 2.05 | 6.68 | 7.64 | 7.85 | 3.65 | 1.77 | 1.42 | 4.68 | 4.23 | 3.96 | 1.4 | 1.24 | 1.03 |
| Resin Type B | 8.84 | 8.01 | 7.97 | 5.62 | 2.79 | 2.35 | 4.56 | 5.01 | 4.74 | 3.2 | 2.33 | 1.43 | 4.41 | 4.63 | 3.17 | 1.78 | 1.42 | 1.33 |
| Resin Type A | 8.65 | 7.71 | 6.83 | 0 | 0 | 0 | 6.78 | 6.75 | 6.47 | 0 | 1.67 | 0.17 | 6.85 | 5.76 | 4.56 | 1.65 | 0.96 | 0 |
| Resin Type D | 7.75 | 7.75 | 7.3 | 0 | 2.92 | 1.91 | 5.01 | 5.32 | 5.64 | 3.62 | 1.77 | 1.35 | 4.44 | 4.96 | 4.21 | 1.25 | 1.05 | 1.06 |
| Resin Type C | 7.26 | 6.63 | 5.36 | 3.69 | 1.96 | 1.91 | 4.73 | 4.71 | 4.49 | 3.28 | 1.59 | 1.44 | 4.55 | 4.48 | 2.74 | 1.8 | 1.29 | 1.32 |
| Resin Type A | 5.73 | 4.28 | 3.6 | 3.36 | 1.6 | 2.03 | 4.68 | 3.56 | 3 | 1.45 | 1.49 | 1.33 | 4.3 | 3.14 | 2.48 | 1.39 | 1.48 | 0.77 |
| Resin Type A | 4.9 | 5.68 | 5.63 | 2.13 | 1.18 | 0.89 | 3.7 | 4.48 | 3.95 | 1.86 | 1.38 | 0.93 | 3.79 | 4.08 | 2.77 | 1.69 | 0.71 | 0.65 |
| Resin Type A | 4.91 | 6.47 | 7.02 | 5.32 | 1.21 | 1.18 | 3.75 | 5.05 | 4.32 | 1.83 | 1.04 | 1 | 3.86 | 3.67 | 3.01 | 1.5 | 0.91 | 0.81 |

| pH | 7.5 | | | | | |
| --- | --- | --- | --- | --- | --- | --- |
| mM NaCl | 5 | 25 | 75 | 100 | 200 | 300 |
| POROS XS | 7.54 | 4.47 | 4.43 | 2.12 | 1.1 | 0.83 |
| Competitor X | 1.99 | 3.55 | 1.49 | 1.67 | 1.02 | 0.69 |
| Competitor Y | 3.23 | 3.77 | 0.94 | 1.34 | 0.7 | 0.51 |
| Resin Type A | 3.38 | 3.82 | 1.25 | 1.48 | 1.1 | 1.2 |
| Resin Type B | 3.74 | 3.54 | 1.33 | 2.18 | 1.24 | 1.19 |
| Resin Type A | 4.41 | 4.62 | 2.29 | 1.41 | 1.08 | 1.1 |

TABLE 2-continued

Selectivity Factor (α) for Cationic Flocculant Resins Types A-D and benchmark resins;
Bold numerals when (α) > 2.5 = good selectivity for aggregate species (HMW); Monomer purified in flow-through mode.

| | 5 | 25 | 75 | 100 | 200 | 300 |
|---|---|---|---|---|---|---|
| Resin Type D | 4.28 | 4.39 | 1.51 | 1.66 | 1.13 | 0.98 |
| Resin Type C | 3.7 | 3.08 | 1.32 | 2.27 | 1.39 | 1.51 |
| Resin Type A | 3.86 | 2.9 | 0.72 | 1.38 | 1.33 | 1.05 |
| Resin Type A | 3.21 | 3.29 | 0.58 | 0.96 | 0.82 | 0.62 |
| Resin Type A | 3.03 | 3.07 | 0.52 | 1.96 | 0.65 | 0.59 |

TABLE 3

Selectivity Factor (α) for Cationic Flocculant Resins Types A-D and benchmark resins;
Bold numerals when (a) > 4.0 = good selectivity for aggregate species (HMW); Monomer purified in flow-through mode.

| pH | 4.5 | | | | | | 5.5 | | | | | | 6.5 | | | | | |
|---|---|---|---|---|---|---|---|---|---|---|---|---|---|---|---|---|---|---|
| mM NaCl | 5 | 25 | 75 | 100 | 200 | 300 | 5 | 25 | 75 | 100 | 200 | 300 | 5 | 25 | 75 | 100 | 200 | 300 |
| POROS XS | 1.05 | 1.39 | 1.73 | 3.67 | 3.1 | 1.75 | 1.71 | 1.21 | 1.7 | 3.86 | 1.99 | 1.26 | 1.96 | 2.45 | 3.51 | 2.62 | 1.35 | 1.06 |
| Competitor X | 0.68 | 0.9 | 1.4 | 0 | 1.91 | 1.27 | 1.57 | 2.34 | 2.27 | 2.28 | 1.2 | 0.94 | 2.11 | 4.77 | 4.04 | 1.94 | 1.17 | 0.94 |
| Competitor Y | 1.93 | 1.82 | 2.48 | 1.81 | 3.35 | 0.89 | 2.6 | 2.91 | 4.39 | 1.4 | 0.98 | 0.84 | 3.44 | 3.9 | 2.19 | 1.65 | 1.13 | 0.92 |
| Ligand Type A | 9.73 | 11.4 | 11.77 | 4.29 | 3.73 | 2.05 | 6.68 | 7.64 | 7.85 | 3.65 | 1.77 | 1.42 | 4.68 | 4.23 | 3.96 | 1.4 | 1.24 | 1.03 |
| Ligand Type B | 8.84 | 8.01 | 7.97 | 5.62 | 2.79 | 2.35 | 4.56 | 5.01 | 4.74 | 3.2 | 2.33 | 1.43 | 4.41 | 4.63 | 3.17 | 1.78 | 1.42 | 1.33 |
| Ligand Type A | 8.65 | 7.71 | 6.83 | 0 | 0 | 0 | 6.78 | 6.75 | 6.47 | 0 | 1.67 | 0.17 | 6.85 | 5.76 | 4.56 | 1.65 | 0.96 | 0 |
| Ligand Type D | 7.75 | 7.75 | 7.3 | 0 | 2.92 | 1.91 | 5.01 | 5.32 | 5.64 | 3.62 | 1.77 | 1.35 | 4.44 | 4.96 | 4.21 | 1.25 | 1.05 | 1.06 |
| Ligand Type C | 7.26 | 6.63 | 5.36 | 3.69 | 1.96 | 1.91 | 4.73 | 4.71 | 4.49 | 3.28 | 1.59 | 1.44 | 4.55 | 4.48 | 2.74 | 1.8 | 1.29 | 1.32 |
| Ligand Type A | 5.73 | 4.28 | 3.6 | 3.36 | 1.6 | 2.03 | 4.68 | 3.56 | 3 | 1.45 | 1.49 | 1.33 | 4.3 | 3.14 | 2.48 | 1.39 | 1.48 | 0.77 |
| Ligand Type A | 4.9 | 5.68 | 5.63 | 2.13 | 1.18 | 0.89 | 3.7 | 4.48 | 3.95 | 1.86 | 1.38 | 0.93 | 3.79 | 4.08 | 2.77 | 1.69 | 0.71 | 0.65 |
| Ligand Type A | 4.91 | 6.47 | 7.02 | 5.32 | 1.21 | 1.18 | 3.75 | 5.05 | 4.32 | 1.83 | 1.04 | 1 | 3.86 | 3.67 | 3.01 | 1.5 | 0.91 | 0.81 |

| pH | 7.5 | | | | | |
|---|---|---|---|---|---|---|
| mM NaCl | 5 | 25 | 75 | 100 | 200 | 300 |
| POROS XS | 7.54 | 4.47 | 4.43 | 2.12 | 1.1 | 0.83 |
| Competitor X | 1.99 | 3.55 | 1.49 | 1.67 | 1.02 | 0.69 |
| Competitor Y | 3.23 | 3.77 | 0.94 | 1.34 | 0.7 | 0.51 |
| Ligand Type A | 3.38 | 3.82 | 1.25 | 1.48 | 1.1 | 1.2 |
| Ligand Type B | 3.74 | 3.54 | 1.33 | 2.18 | 1.24 | 1.19 |
| Ligand Type A | 4.41 | 4.62 | 2.29 | 1.41 | 1.08 | 1.1 |
| Ligand Type D | 4.28 | 4.39 | 1.51 | 1.66 | 1.13 | 0.98 |
| Ligand Type C | 3.7 | 3.08 | 1.32 | 2.27 | 1.39 | 1.51 |
| Ligand Type A | 3.86 | 2.9 | 0.72 | 1.38 | 1.33 | 1.05 |
| Ligand Type A | 3.21 | 3.29 | 0.58 | 0.96 | 0.82 | 0.62 |
| Ligand Type A | 3.03 | 3.07 | 0.52 | 1.96 | 0.65 | 0.59 |

TABLE 4

Selectivity Factor (α) for Cationic Flocculant Resins Types A-D and some benchmarking resins;
Bold numerals when (α) < 0.9 = good selectivity for monomer; Monomer purified in bind-elute mode.

| pH | 4.5 | | | | | | 5.5 | | | | | | 6.5 | | | | | |
|---|---|---|---|---|---|---|---|---|---|---|---|---|---|---|---|---|---|---|
| mM NaCl | 5 | 25 | 75 | 100 | 200 | 300 | 5 | 25 | 75 | 100 | 200 | 300 | 5 | 25 | 75 | 100 | 200 | 300 |
| POROS XS | 1.05 | 1.39 | 1.73 | 3.67 | 3.1 | 1.75 | 1.71 | 1.21 | 1.7 | 3.86 | 1.99 | 1.26 | 1.96 | 2.45 | 3.51 | 2.62 | 1.35 | 1.06 |
| Competitor X | 0.68 | 0.9 | 1.4 | 0 | 1.91 | 1.27 | 1.57 | 2.34 | 2.27 | 2.28 | 1.2 | 0.94 | 2.11 | 4.77 | 4.04 | 1.94 | 1.17 | 0.94 |
| Competitor Y | 1.93 | 1.82 | 2.48 | 1.81 | 3.35 | 0.89 | 2.6 | 2.91 | 4.39 | 1.4 | 0.98 | 0.84 | 3.44 | 3.9 | 2.19 | 1.65 | 1.13 | 0.92 |
| Ligand Type A | 9.73 | 11.4 | 11.77 | 4.29 | 3.73 | 2.05 | 6.68 | 7.64 | 7.85 | 3.65 | 1.77 | 1.42 | 4.68 | 4.23 | 3.96 | 1.4 | 1.24 | 1.03 |
| Ligand Type B | 8.84 | 8.01 | 7.97 | 5.62 | 2.79 | 2.35 | 4.56 | 5.01 | 4.74 | 3.2 | 2.33 | 1.43 | 4.41 | 4.63 | 3.17 | 1.78 | 1.42 | 1.33 |
| Ligand Type A | 8.65 | 7.71 | 6.83 | 0 | 0 | 0 | 6.78 | 6.75 | 6.47 | 0 | 1.67 | 0.17 | 6.85 | 5.76 | 4.56 | 1.65 | 0.96 | 0 |
| Ligand Type D | 7.75 | 7.75 | 7.3 | 0 | 2.92 | 1.91 | 5.01 | 5.32 | 5.64 | 3.62 | 1.77 | 1.35 | 4.44 | 4.96 | 4.21 | 1.25 | 1.05 | 1.06 |
| Ligand Type C | 7.26 | 6.63 | 5.36 | 3.69 | 1.96 | 1.91 | 4.73 | 4.71 | 4.49 | 3.28 | 1.59 | 1.44 | 4.55 | 4.48 | 2.74 | 1.8 | 1.29 | 1.32 |
| Ligand Type A | 5.73 | 4.28 | 3.6 | 3.36 | 1.6 | 2.03 | 4.68 | 3.56 | 3 | 1.45 | 1.49 | 1.33 | 4.3 | 3.14 | 2.48 | 1.39 | 1.48 | 0.77 |
| Ligand Type A | 4.9 | 5.68 | 5.63 | 2.13 | 1.18 | 0.89 | 3.7 | 4.48 | 3.95 | 1.86 | 1.38 | 0.93 | 3.79 | 4.08 | 2.77 | 1.69 | 0.71 | 0.65 |
| Ligand Type A | 4.91 | 6.47 | 7.02 | 5.32 | 1.21 | 1.18 | 3.75 | 5.05 | 4.32 | 1.83 | 1.04 | 1 | 3.86 | 3.67 | 3.01 | 1.5 | 0.91 | 0.81 |

TABLE 4-continued

Selectivity Factor (α) for Cationic Flocculant Resins Types A-D and some benchmarking resins;
Bold numerals when (α) < 0.9 = good selectivity for monomer; Monomer purified in bind-elute mode.

| pH | 4.5 | | | | | | 5.5 | | | | | | 6.5 | | | | | |
|---|---|---|---|---|---|---|---|---|---|---|---|---|---|---|---|---|---|---|
| mM NaCl | 5 | 25 | 75 | 100 | 200 | 300 | 5 | 25 | 75 | 100 | 200 | 300 | 5 | 25 | 75 | 100 | 200 | 300 |

| | pH | 7.5 | | | | | |
|---|---|---|---|---|---|---|---|
| | mM NaCl | 5 | 25 | 75 | 100 | 200 | 300 |
| | POROS XS | 7.54 | 4.47 | 4.43 | 2.12 | 1.1 | 0.83 |
| | Competitor X | 1.99 | 3.55 | 1.49 | 1.67 | 1.02 | 0.69 |
| | Competitor Y | 3.23 | 3.77 | 0.94 | 1.34 | 0.7 | 0.51 |
| | Ligand Type A | 3.38 | 3.82 | 1.25 | 1.48 | 1.1 | 1.2 |
| | Ligand Type B | 3.74 | 3.54 | 1.33 | 2.18 | 1.24 | 1.19 |
| | Ligand Type A | 4.41 | 4.62 | 2.29 | 1.41 | 1.08 | 1.1 |
| | Ligand Type D | 4.28 | 4.39 | 1.51 | 1.66 | 1.13 | 0.98 |
| | Ligand Type C | 3.7 | 3.08 | 1.32 | 2.27 | 1.39 | 1.51 |
| | Ligand Type A | 3.86 | 2.9 | 0.72 | 1.38 | 1.33 | 1.05 |
| | Ligand Type A | 3.21 | 3.29 | 0.58 | 0.96 | 0.82 | 0.62 |
| | Ligand Type A | 3.03 | 3.07 | 0.52 | 1.96 | 0.65 | 0.59 |

In summary: Where the selectivity factor, alpha, is greater than 1 the aggregate preferentially binds to the resin compared to the monomer. Under these conditions, flow through mode of purification is preferred. In order to obtain high purity, the selectivity factor should be maximized. A selectivity factor of greater than 2.5 is desired whereas a selectivity factor of 4.5 is preferred.

Where the selectivity factor, alpha, is less than 1 the monomer preferentially binds to the resin compared to the aggregate. Under these conditions bind and elute mode of purification is preferred. In order to obtain high purity, the selectivity factor should be maximized. A selectivity factor of lesser than 0.9 is desired.

Due to molecular diffusion and differences in partition coefficients for minor post translational modifications, a selectivity factor close to 1 may result in reduced purity. Where the selectivity factor is 1, there will be no separation of the target (for e.g., monomer) and impurity.

Figure 3A:
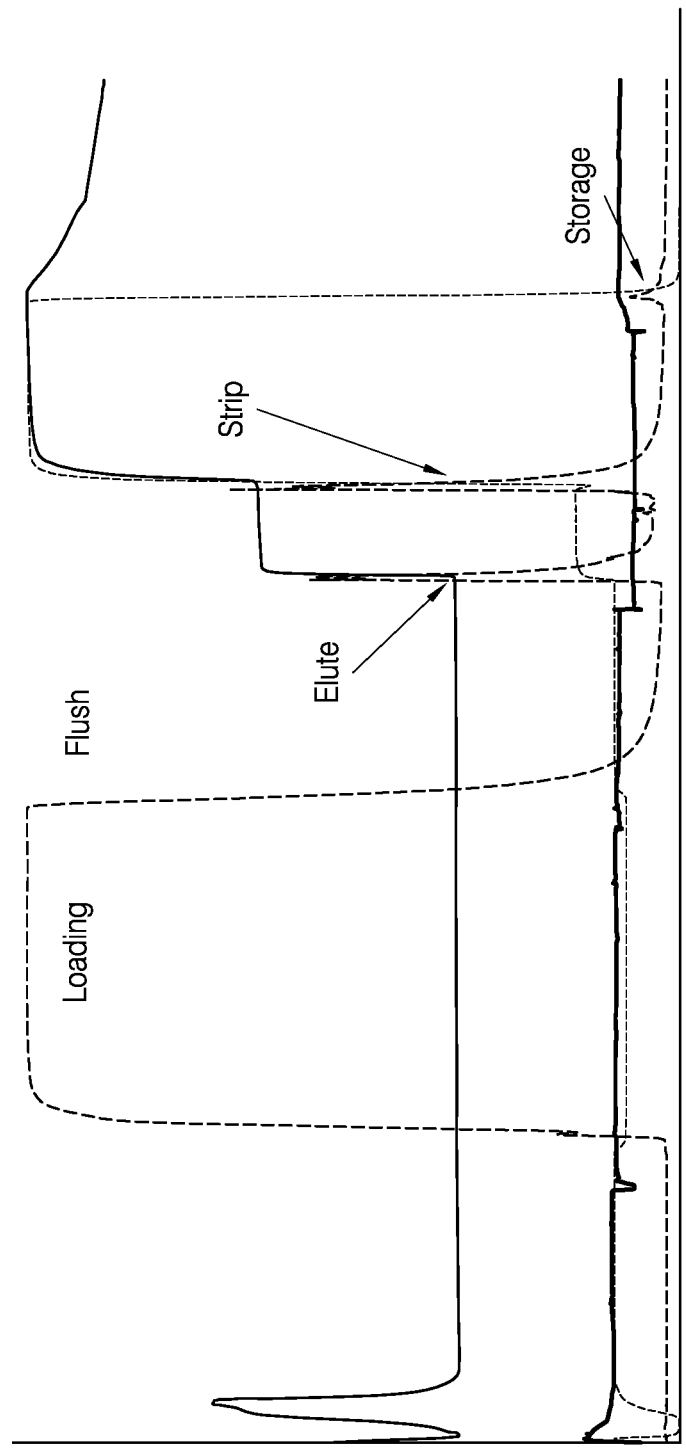
FIG. 3a shows an expanded Size Exclusion Chromatogram of fractions taken from the purification profile for Resin B is shown.
Figure 3B:
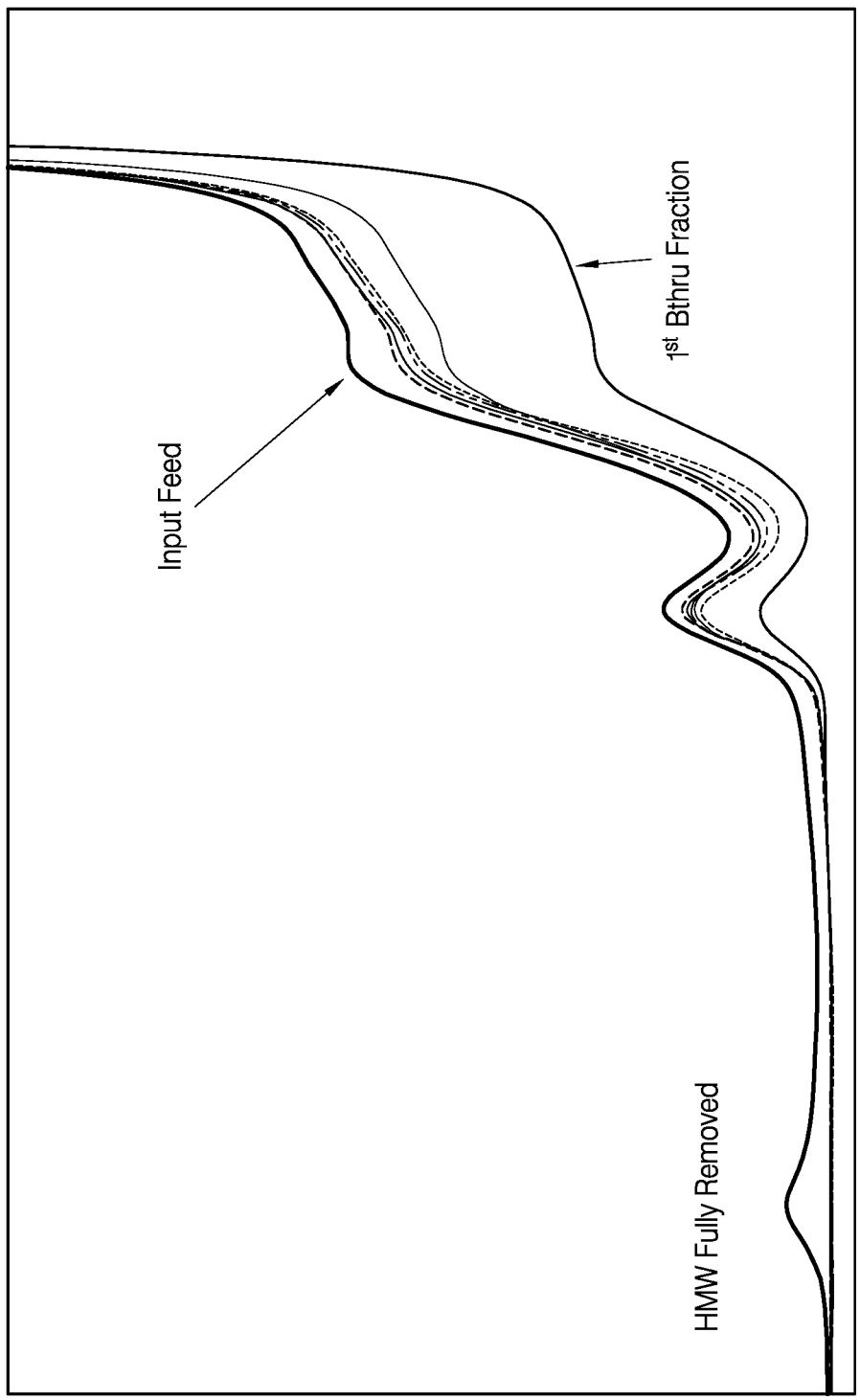
FIG. 3b shows the chromatograms of various fractions from the run of FIG. 3a. In the breakthrough fraction, there is good removal of most species, with the HMW species being completely removed across the entire run, and other HMW species being reduced.

Example 3: Removal of Aggregate Species Across Various Types of Flocculant Resins Certain flocculant resins were tested under various purification conditions. In FIG. 3a, resin B was used as the separation medium, and the expanded Size Exclusion Chromatogram of fractions taken from the purification profile for Resin B is shown (FIG. 3b). This is a standard method to determine aggregate removal of a variety of aggregate species (HMW, LMW) and cumulative monomer purity. Briefly, the antibody feed solution (load) is pumped onto the column comprising resin B under various pH conditions pH 4.5, 5.0 and 5.5. Flush=when the load antibody solution is switched and the tubing is flushed/washed with loading buffer. A salt solution in Tris buffer at pH 8.0 was used as the elution buffer. Strip=NaOH cleansing of column prior to regeneration and storage.

In FIG. 3b, the chromatograms of various fractions from the run of FIG. 3a is shown. The top curve (input feed) shows the starting material before purification, comprising significant amounts of various HMW aggregate species. In the breakthrough fraction, there is good removal of most species, with the HMW species being completely removed across the entire run, and other HMW species being reduced. Due to the high degree of binding of the HMW to the column it is effectively removed. The % recovery of the flow-through antibody is shown below in Table 5. Monomer shows excellent recovery (>90%) in flow through mode at pH 4.5, 5.0 and 5.5.

TABLE 5

% Recovery of the flow-through antibody for Resin B
Yield

| Load pH | pH 4.5 | pH 5.0 | pH 5.5 |
|---|---|---|---|
| FT | 93.95% | 94.60% | 94.53% |
| Eluate | 2.18% | 2.84% | 2.60% |
| Strip (Calculated) | 3.10% | 3.39% | 3.10% |
| Total | 99.23% | 100.83% | 100.23% |

Figures 4A, 4B, 4C:
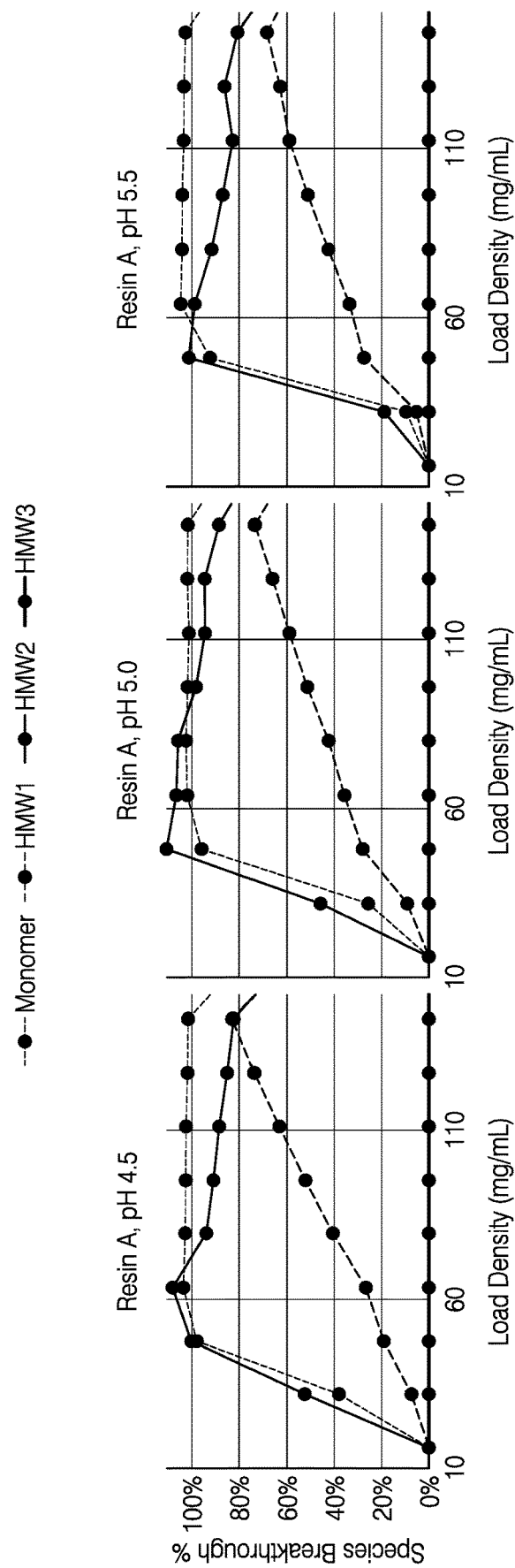
FIG. 4A, FIG. 4B, and FIG. 4C show purification data from Resin A, displayed as antibody breakthrough curves, each at pH 4.5, 5.0 and 5.5.
Figures 4D, 4E, 4F:
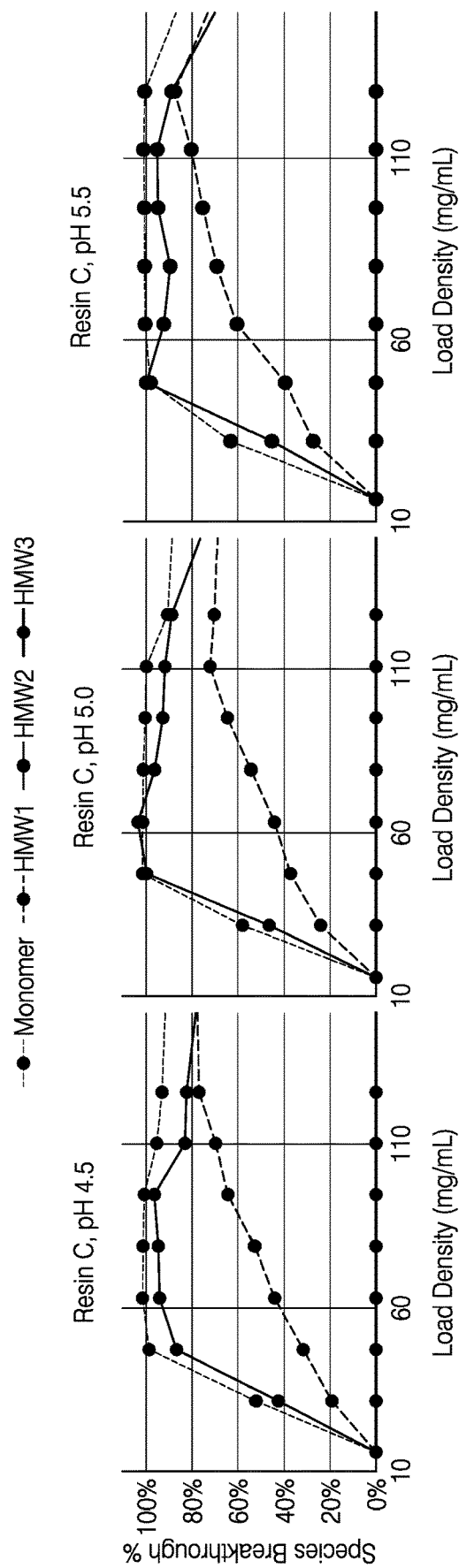
FIG. 4D, FIG. 4E, and FIG. 4F show purification data from Resin C, displayed as antibody breakthrough curves, each at pH 4.5, 5.0 and 5.5.

FIGS. 4a and 4b show purification data from Resin A and Resin C respectively, displayed as antibody breakthrough curves, each at pH 4.5, 5.0 and 5.5. The two flocculant ligand types Resin A and Resin C show consistent and effective removal of high molecular weight species HMW3. While the monomer seems to have similar selectivity as HMW2, another high molecular wt. species HMW1 is gradually removed by these resins.

Figure 5A:
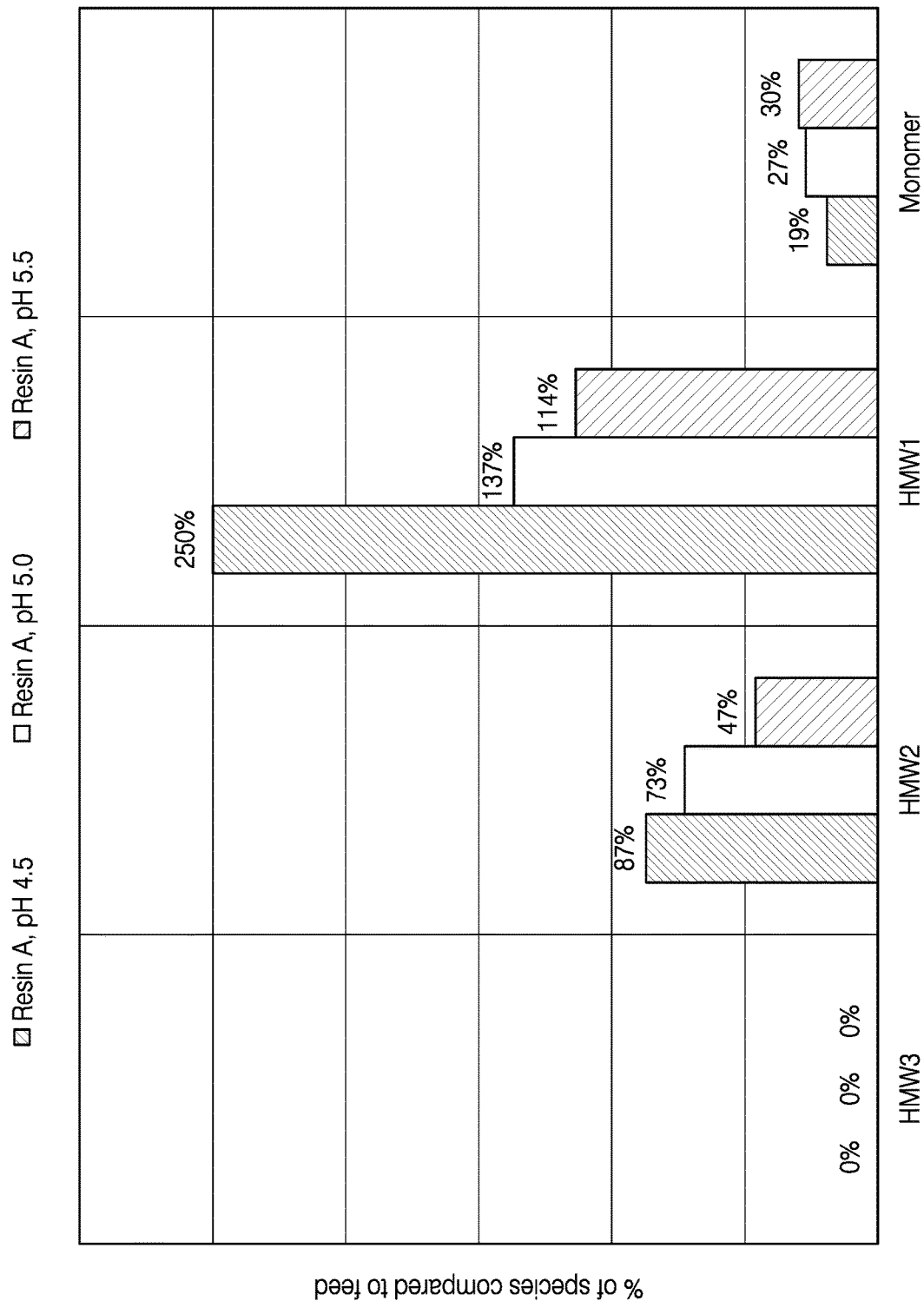
FIGS. 5a and 5b show elution analysis with 1M Tris buffer at pH 8.5, for Resin A and Resin C respectively. Fraction compositions, as determined by size exclusion chromatogram (SEC), show the removal of higher molecular weight species through binding to the resins. Selectivity is pH dependent. Tris elution shows significant removal of the dimer species but very little monomer loss. HMW species is bound tightly to the resins, showing excellent selectivity for this species.
Figure 5B:
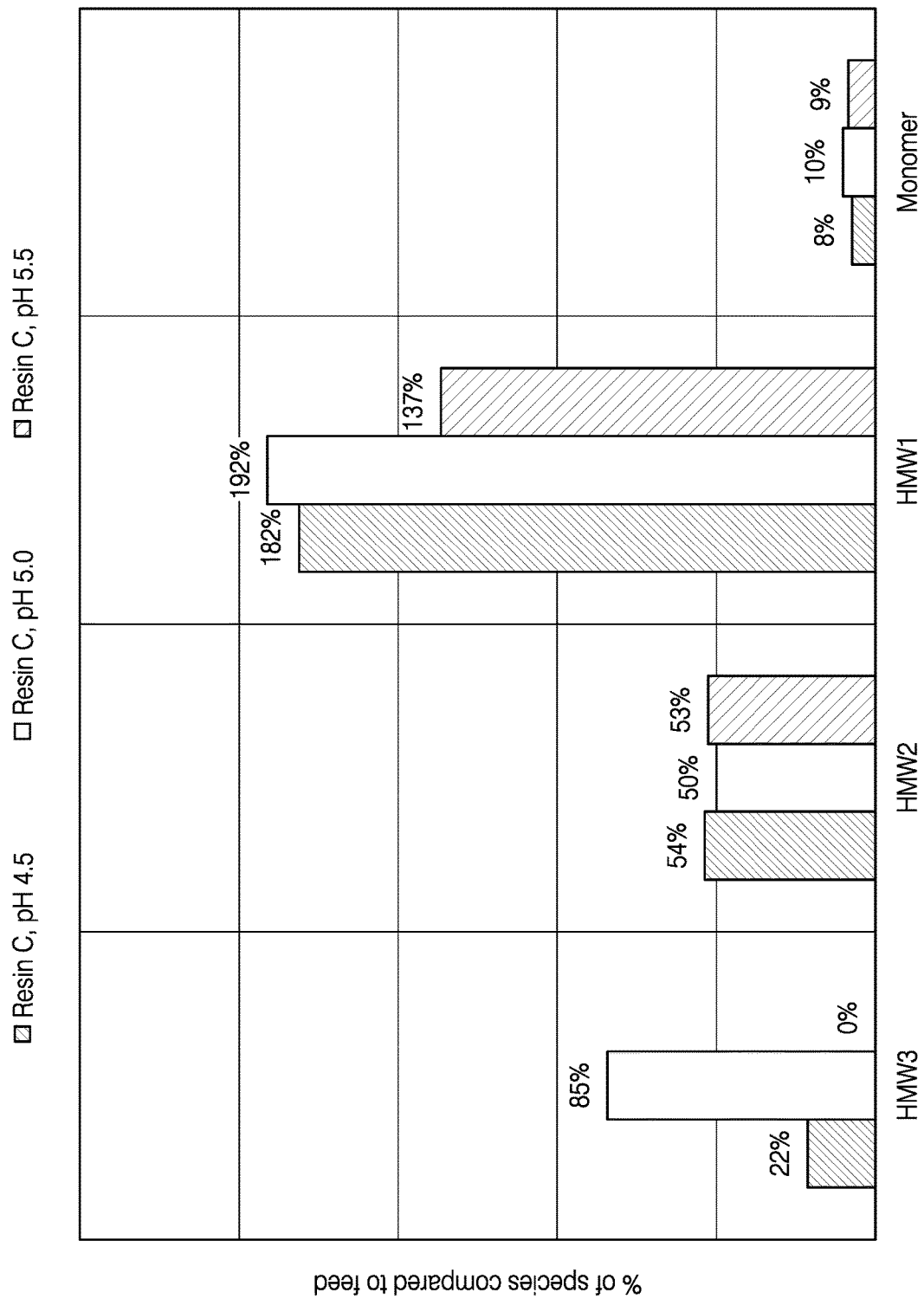

FIGS. 5a and 5b show elution analysis with 1M Tris buffer at pH 8.5, for Resin A and Resin C. The resins were loaded with an antibody solution each at pH 4.5, 5.0 and 5.5. Resin A was very effective in removing HMW3 completely. Tris elution shows significant removal of the HMW1 species and very little monomer loss. HMW3 is bound tightly, especially for resin A which shows excellent selectivity for this species.

Example 4: Exemplary Anion Exchange (AEX) Flocculant Resins

In order to reduce production costs, resins are typically reused by biomanufacturing plants. To make reuse possible, these materials are cleaned, sanitized and stored in a bacteriostatic solution, a process that takes time, increases costs and has validation implications. Antimicrobial solutions such as acidic and basic buffers, as well as 20% ethanol may be used. Currently there is an increasing trend to move away from ethanol storage due to safety concerns (flammable), hence storage in alkaline solutions is increasing.

Purification resins having inherent antimicrobial and/or bacteriostatic properties allow resin storage in buffer or water. Additionally, if such resins also have specific functionality for capture or polish operations, it would be a significant benefit to customers.

Antimicrobial and bacteriostatic surface chemistries are known in many industries. We engineered base resins by adding antimicrobial and bacteriostatic flocculant surface chemistries. Examples of such chemistries include but not limited to, molecules such as organic acids, short chain alcohols and benzyl alcohol, etc. which show excellent base stability. Exemplary antimicrobial and cationionic flocculant polymers include but are not limited to, Tris(2-aminoethyl) amine, Tris(3-aminopropyl)amine, linear polyethyl amines of varying chain lengths, and polyethyleneimine, poly(N-vinylpyrrolidone) (PVP), quaternary aminated polyacrylates, poly(N,N-dimethylpiperidinium chloride), poly (DADMAC) (Polydiallyldimethylammonium chloride), etc. Other potential solutions include antimicrobials from the personal care industry, including but not limited to, Triclosan, antimicrobial peptides and proteins that destabilize the biological membrane, etc. These chemistries may also result in having unique selectivity's or affinities, for e.g., for biotheraputics.

In exemplary embodiments, primary, secondary, tertiary, quaternary amines, poly(DADMAC), etc. were conjugated to porous resins.

AEX resin 1 comprises a poly(styrene-co-divinylbenzene) bead with a modal pore size of around 200 nm and a hydrophilic coating, functionalized with an amine, resulting in a surface comprising primary, secondary and tertiary amines.

AEX resin 2 comprises a poly(styrene-co-divinylbenzene) bead with a modal pore size of around 100 nm and hydrophilic coating, functionalized with the flocculant poly (DADMAC), resulting in a fully ionized quaternary amine surface.

AEX resin 3 comprises a poly(styrene-co-divinylbenzene) bead with a modal pore size of around 200 nm and hydrophilic coating, functionalized with a PEI-like polymer resulting in a surface comprising primary, secondary, tertiary amines and quaternary amines.

AEX resin 4 comprises a poly(methacrylate) bead with a modal pore size of around 500 nm functionalized with an amine resulting in a surface comprising primary, secondary, tertiary amines and quaternary amines.

AEX resin 5 comprises a poly(styrene-co-divinylbenzene) bead with a modal pore size of around 40 nm and hydrophilic coating, functionalized with the flocculant poly (DADMAC) resulting in a fully ionized quaternary amine surface.

AEX resin 6 comprises a poly(styrene-co-divinylbenzene) bead with a modal pore size of around 200 nm and hydrophilic coating, functionalized with the flocculant poly (DADMAC) resulting in a fully ionized quaternary amine surface.

We successfully demonstrated the use of AEX resins 1-6 in purification data for the removal of impurities (DNA: see FIG. 7), and for the separation of product related variants based on protein modifications including but not limited to glycosylation, sialylation, phosphorylation and N-terminal acetylation (FIGS. 6a, 6b, 6c, 6d and 6e).

The AEX resins described above can also be evaluated for microbial growth inhibition and bioburden testing in a range of non-bacteriostatic solutions.

Example 5: Properties of Anion Exchange (AEX) Flocculant Resins

In order to demonstrate the preferential binding properties of the AEX resins, ovalbumin was used as a test molecule and was subjected to a bind—elute type purification on the AEX flocculant resins. Ovalbumin is a 42.7 kDa protein, comprising 385 amino acids, with a serpin-like structure. Commercially available ovalbumin when purified by precipitation contains several modifications or charge variants that can be considered product related impurities. Modifications or charge variants include, but are not limited to glycosylated, glycated, oxidized, deaminated, acidic, basic, phosphorylated, sialylated or a N-terminal acetylated forms, etc. and they result in a mixture of closely related species that need separation. The AEX flocculant resins described herein may use pH-based gradients for the resolutions and/or separation of charge variants of the peptide/protein/antibody/product.

Cationic flocculant ligands are typically polyelectrolytes either formed prior to binding to the surface or created while in one or multipole reaction the polyelectrolyte is bound to the surface. Copolymer are used to modulate the charge in order to achieve the desired impurity removal selectivity.

Figure 6A:
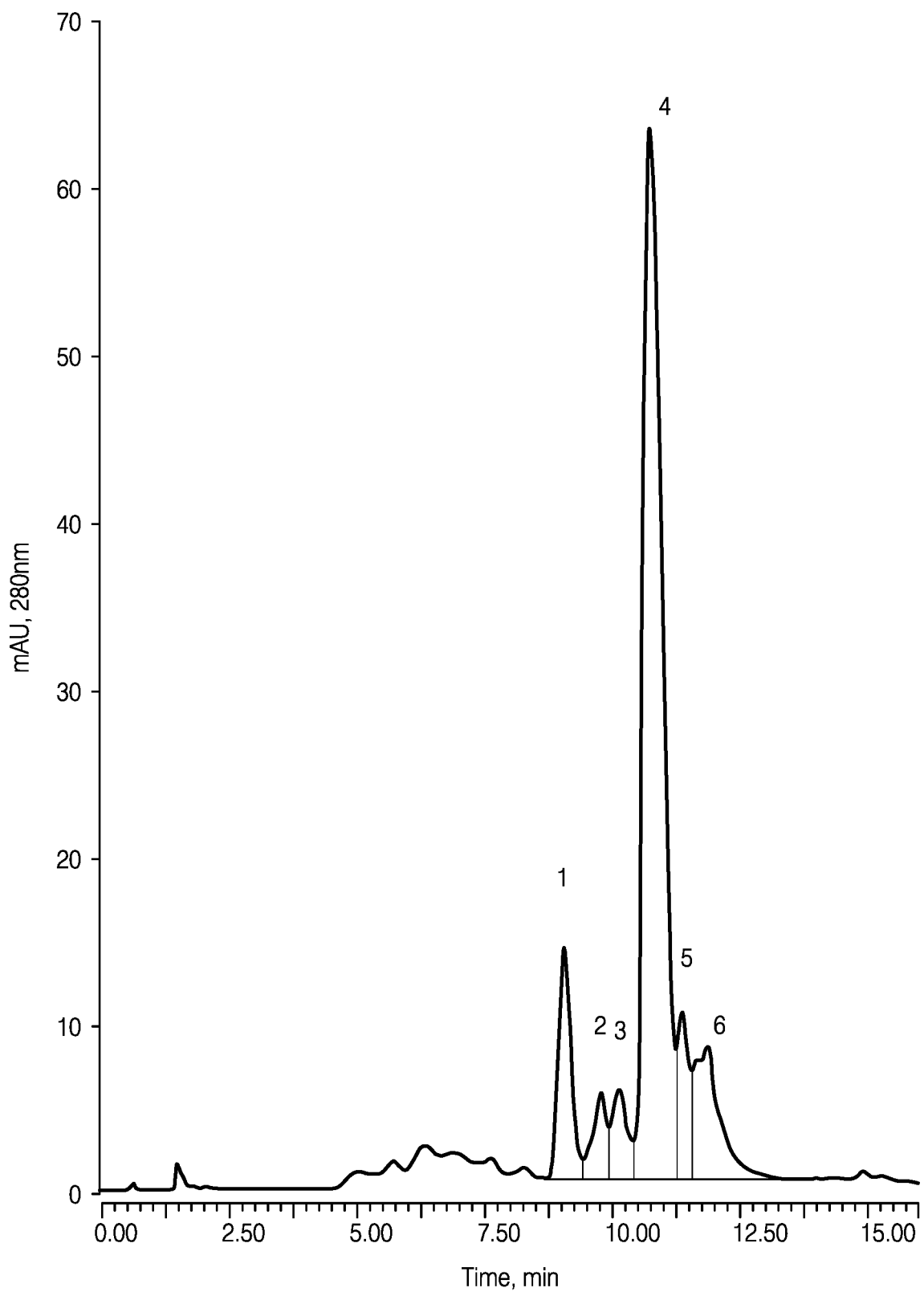
FIG. 6a: shows a chromatographic line graph of variants of ovalbumin, when an ovalbumin sample is injected onto and separated using an analytical HPLC column (Thermo Scientific ProPac SAX-10). Each peak represents a variant ovalbumin (difference in glycosylation, sialylation, etc.) or a group of variants not resolved on this column (labelled peaks 1-6).
Figure 6B:
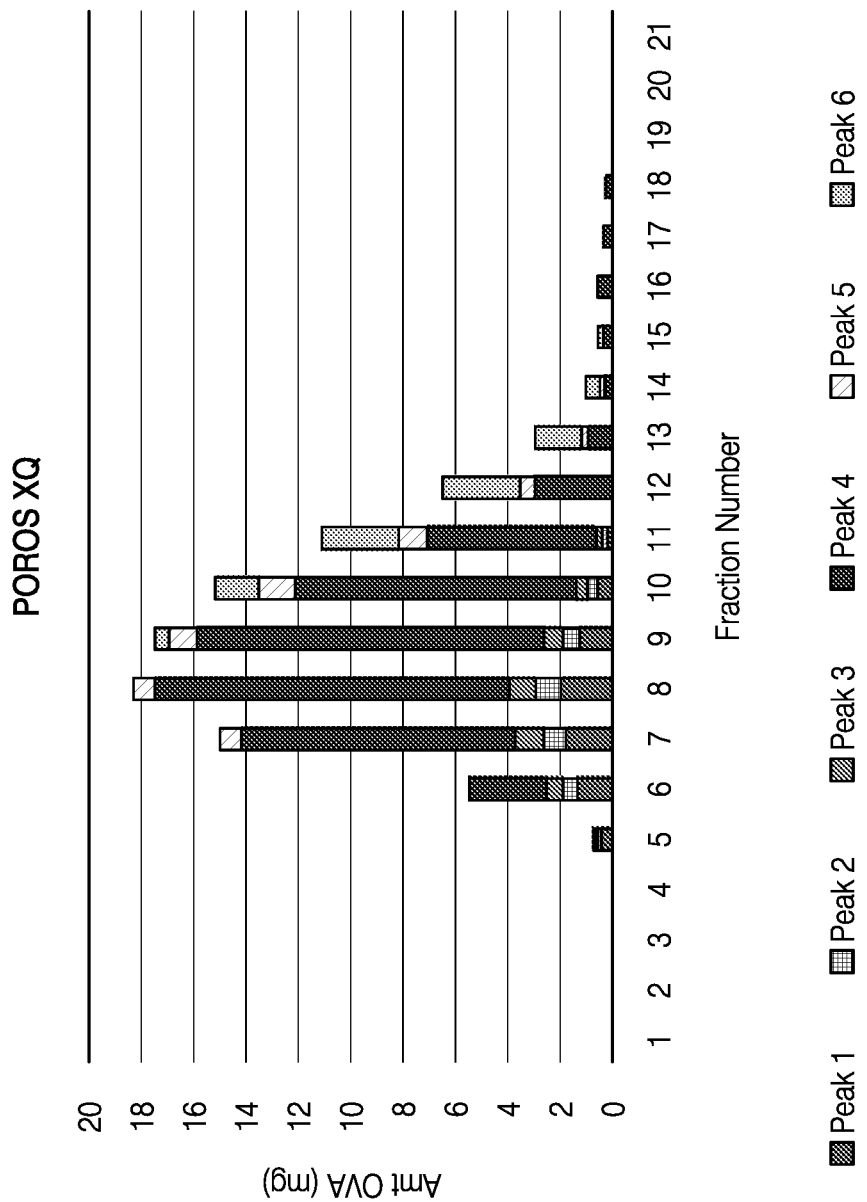
FIGS. 6b, 6c, 6d and 6e show the HPLC profile of ovalbumin variants in each fraction as a stacked bar graphs.
Figure 6C:
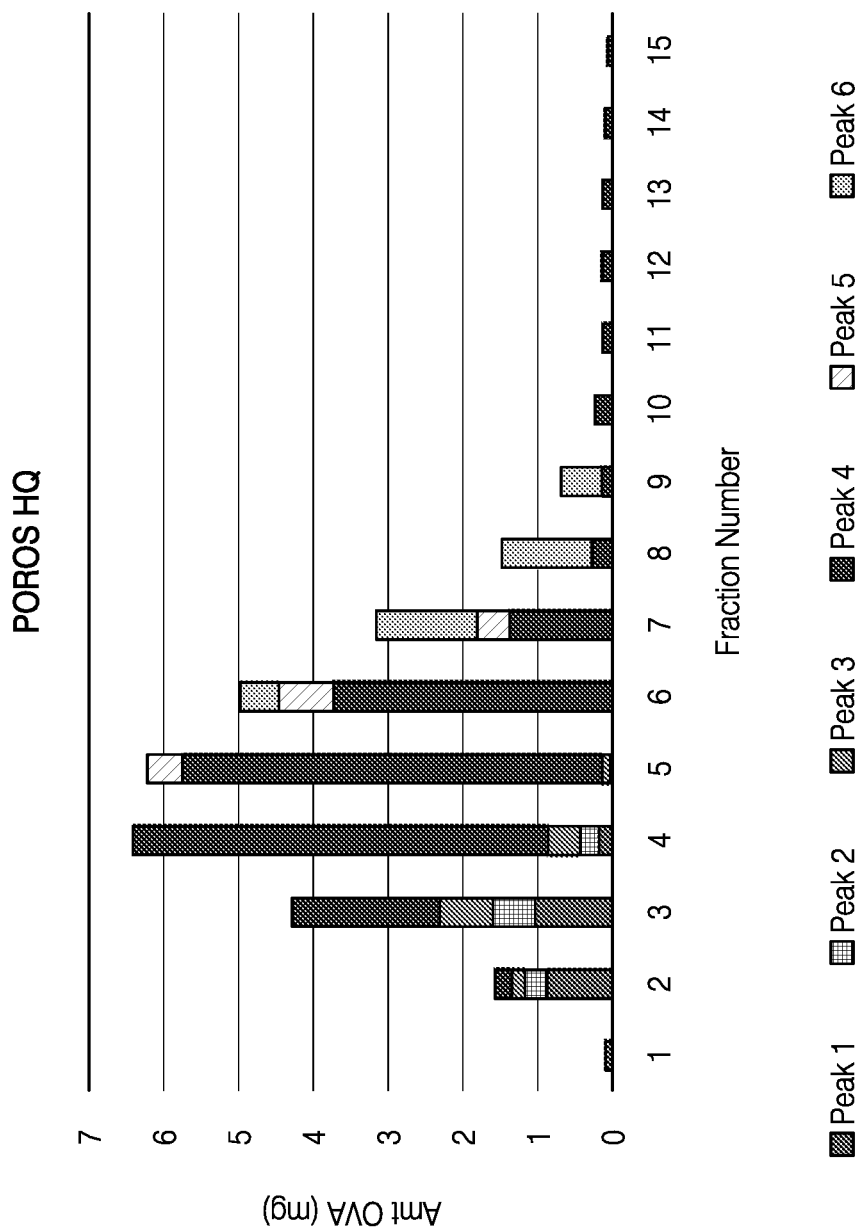
Figure 6D:
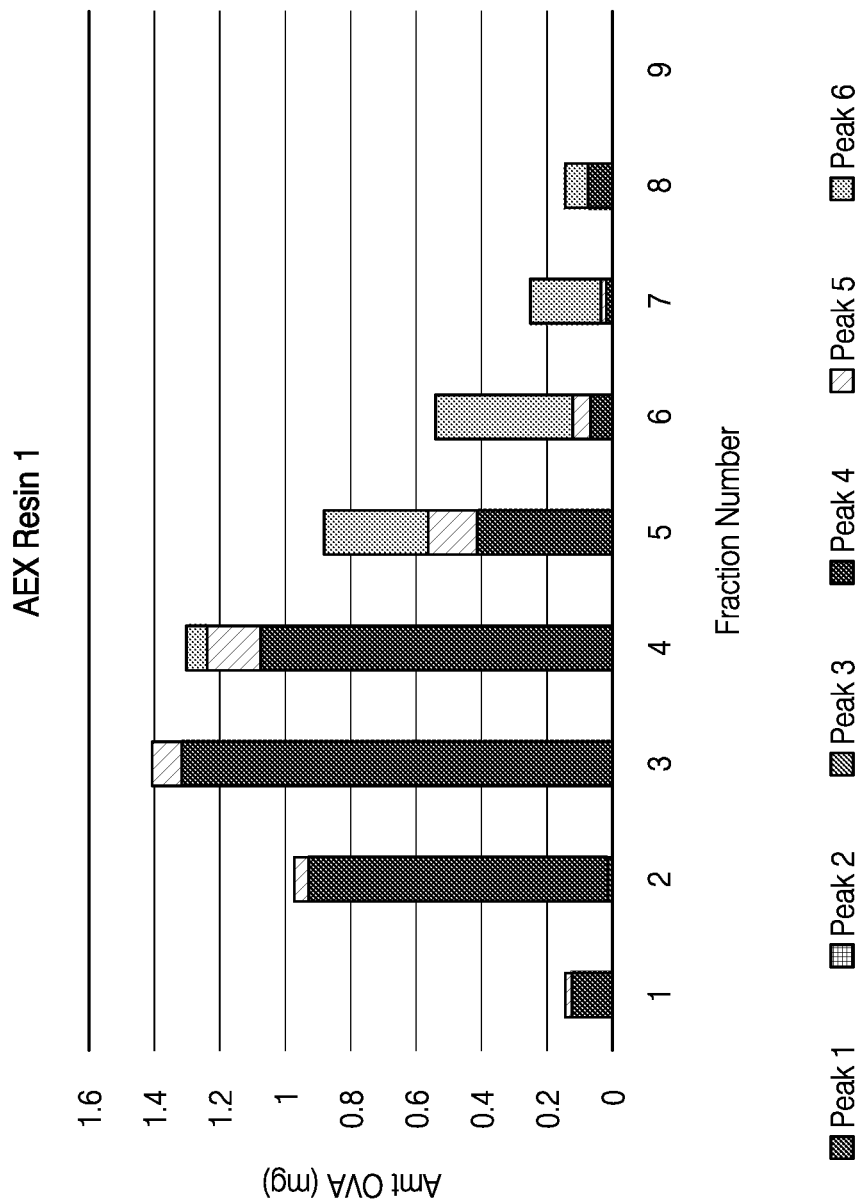
Figure 6E:
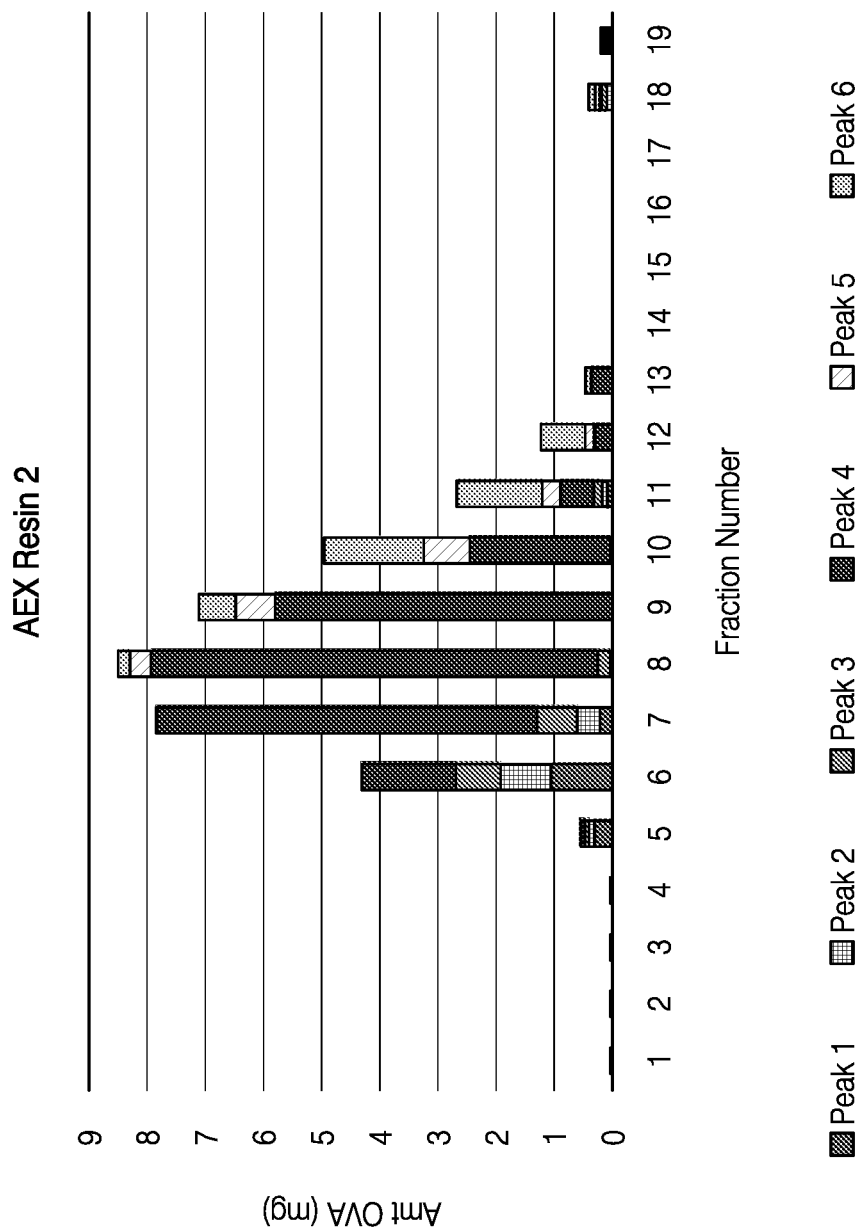

In FIG. 6a, the chromatographic panel shows the variant profile of ovalbumin when injected onto and separated using an analytical HPLC column (Thermo Scientific ProPac SAX-10). Each peak represents a variant or group of variants not resolved on this column (labelled peaks 1-6).

To assess the selectivity of each of the anion exchange resins (AEX) synthesized in this disclosure, AEX resins 1 and 2 were compared to the commercially available AEX resins (POROS XQ and POROS HQ). In this experiment, a feed solution of ovalbumin was loaded onto the resin in column format until 5% break through occurred. At this point an elution gradient from 0 to 1M sodium chloride was applied. Fractions were collected from the start of the gradient. The same method was used for each test. Each fraction was then analyzed by HPLC. Each peak was identified in comparison to the feed and the composition of each fraction determined. Each FIGS. 6b, 6c, 6d and 6e show the composition of each fraction as a stacked bar graph. In the case of AEX resin 1 (FIG. 6d), peak components 1, 2 and 3 were not selectively bound to the column and did not appear in the fraction analysis. In contrast, AEX resin 2 (FIG. 6e) shows retention of these components into fraction 8 as well as increased retention of other species when compared to commercial AEX resins POROS XQ (FIG. 6b) and POROS HQ (FIG. 6c) not based on flocculant chemistry. The differences in profiles demonstrate that the AEX resins have differential selectivity of each resin chemistry.

In order to assess base stability resins 1, 2, 3, 5 and 6 were stored in 1M NaOH$_{(aq)}$ at 40° C. for 7 days. After which the resins were washed with water until neutral. Ionic capacity was measured before and after storage. Results are shown below in Table 6.

TABLE 6

Properties of the AEX Flocculant Resins.

| Resin | Initial Surface Ionization (μmol/mL resin) | Post Surface Ionization (μmol/mL resin) |
| --- | --- | --- |
| AEX Resin 1 | 37 | 33 |
| AEX Resin 2 | 22 | 21 |
| AEX Resin 3 | 212 | 205 |
| AEX Resin 5 | 63 | 65 |
| AEX Resin 6 | 12 | 11 |

Figure 7:
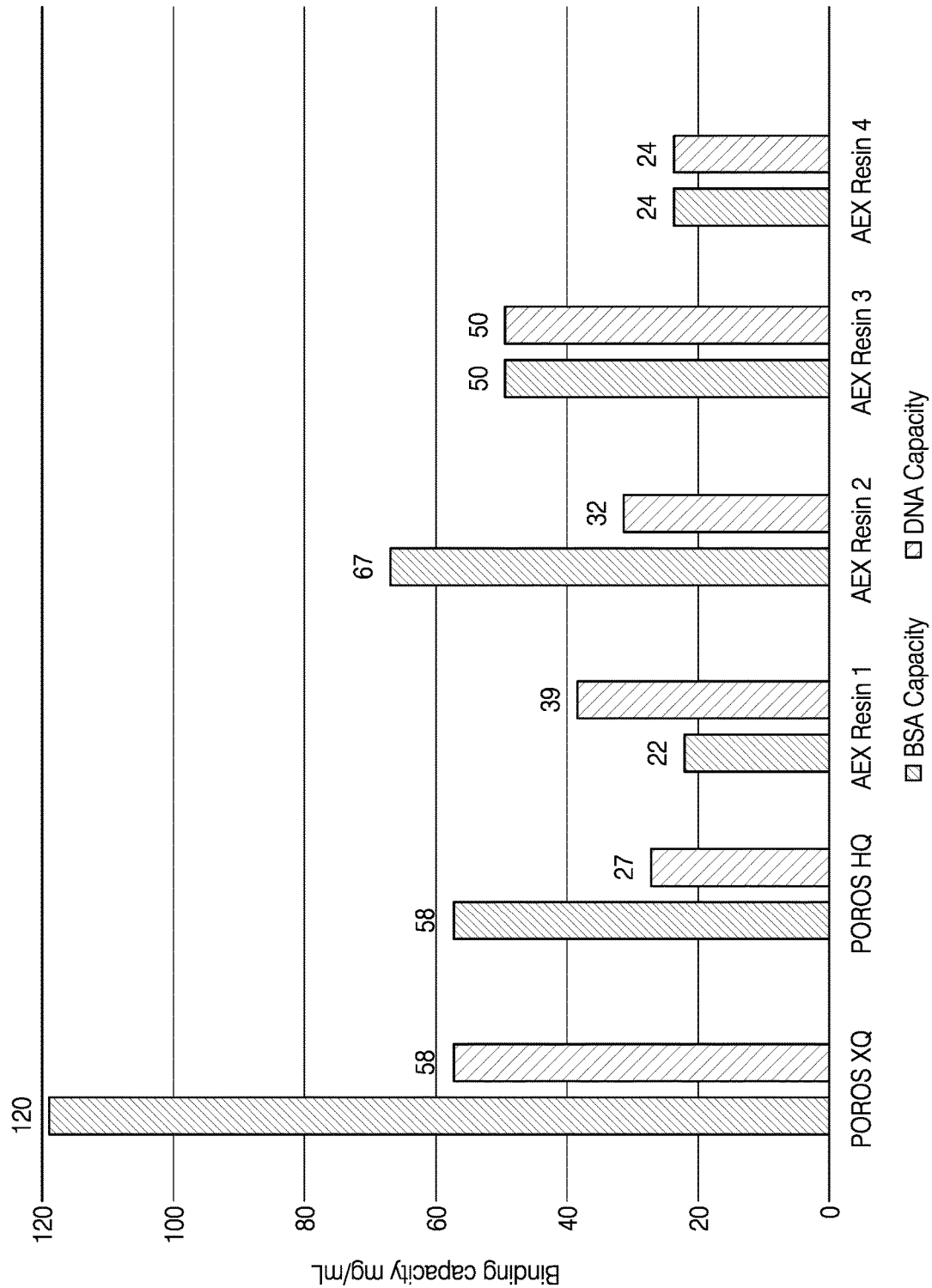
FIG. 7: DNA versus protein binding capacity of AEX Resins 1, 2, 3, and 4 versus commercial, non-flocculant, anionic exchange resins—POROS XQ control and POROS HQ control.

The binding capacity of the AEX resins was also characterized using a mixture of bovine serum albumin and DNA, to evaluate nucleic acid binding of the AEX resins. It is known that resins with an increase surface area can be expected to bind a higher amount of protein per unit area. FIG. 7 shows a comparable ratio of binding for POROS XQ and POROS HQ as well as resin 2, indicating comparable ability to remove host cell DNA from the feed solution. Resin 1, 3 and 4 show differentiated binding characteristics with an increase capability to remove DNA compared to BSA.

Future Applications are anticipated for the flocculant functional chemistries described herein, on surfaces described throughout the disclosure. The flocculant CEX resins of this disclosure can be used in a variety of application, for e.g., a) an analytical separation and/or screening tool; b) for large scale purification, for e.g., polish strategy; c) addition of flocculant resins to stirred tanks to enhance flocculation of impurities (or target, as applicable) for easy separation of a class of ligate species that selectively bind the flocculant resin; d) application of the flocculant chemistries described to new surfaces including but not limited to: hollow fibers, membranes, nanofibers, to a bioreactor including a Single Use bag or container, etc. for novel applications; e) holding a molecule upstream in a container, etc.

What is claimed is:

1. An anion exchange separation medium comprising:
   a. a base surface; and
   b. at least one cationic flocculant ligand covalently attached to the base surface, wherein the cationic flocculant ligand is an aliphatic, heterocyclic, or arylalkyl compound comprising at least one substituent group selected from hydrazide, an imidazole, an oxime, a hydrazine, hydrazone, N-vinylpyrrolidone, and piperidinium.

2. The separation medium of claim 1, wherein the at least one cationic flocculant ligand comprises a cationic group.

3. The separation medium of claim 1, wherein the separation medium is contacted with a solution, a feed or an eluent that comprises one or more ligate species, under operating conditions that allow the binding of at least one ligate species from the solution, feed or eluent, to the separation medium, wherein the one or more ligate species is a mixture of biological substances, wherein the mixture of biological substances comprises a target molecule and at least one impurity.

4. The separation medium of claim 3, wherein the impurity is an aggregate, and the target molecule is either a monomeric antibody, a therapeutic peptide or protein, a virus or viral particle, a particular variant of a peptide or protein or antibody or virus or viral particle, or a nucleic acid.

5. The separation medium of claim 1, wherein the separation medium selectively binds an antibody monomer, and wherein the separation medium has a separation factor (a) of less than 1.

6. The separation medium of claim 5, wherein the antibody monomer is separated from one or more aggregates with the separation medium having a separation factor (a) of at least about 0.1 to about 0.9.

7. The separation medium of claim 2, wherein the cationic flocculant ligand is an aliphatic hydrazide, an imidazole, an aliphatic oxime, an aliphatic hydrazine, an aliphatic hydrazone, or a cationic polyelectrolyte.

8. The separation medium of claim 2, wherein the cationic flocculant ligand is poly(N,N-dimethylpiperidinium chloride) or poly(N-vinylpyrrolidone) (PVP).

9. The separation medium of claim 1, wherein the separation medium can selectively bind to an impurity, and/or, wherein the impurity is a nucleic acid, and/or, wherein the charged variant are is a glycosylated, a glycated, an oxidized, a deaminated, an acidic, a basic, a phosphorylated, a sialylated or a N-terminal acetylated form.

10. The separation medium of claim 1, wherein the base surface comprises a resin, bead, sphere, particle, microcarrier, membrane, web, bag, bioreactor, tube, plate, array, flat surface, filter, fiber or a fabric.

11. The separation medium of claim 1, wherein the base surface is porous, nonporous, microporous, woven, nonwoven, polymeric, non-polymeric, fibrous or winged, and the base surface comprises a material selected from ceramics, glass, metal, silica, synthetic polymeric materials such as styrene, acrylate, acrylamide, acrylamide containing one or more polymerizable vinyl groups, polymeric monoliths, natural polymers, such as cellulose, lignocellulose or their derivatives, agarose, and a combination of any of these materials.

12. A method of separating a monomer and least one aggregate comprising;
   i. providing a separation medium according to claim 1; and
   ii. passing a solution, an eluent, or a feed comprising one or more biological substances through
   the separation medium at a rate sufficient to allow at least one soluble molecule to bind to the separation medium.

13. A method of purifying a protein of interest from a solution, an eluent, or a feed comprising:
   i. providing a separation medium according to claim 1; and
   ii. passing the solution, eluent, or feed comprising the protein of interest and one or more
   impurities through the separation medium at a rate sufficient to allow the one or more impurities to bind
   to the separation medium.

14. An anion exchange separation medium comprising:
   a. a base surface; and
   b. at least one cationic flocculant ligand covalently attached to the base surface, wherein the cationic flocculant ligand is a heterocyclic or arylalkyl compound that comprises a group selected from amine, hydrazide, imidazole, oxime, hydrazine, hydrazone, N-vinylpyrrolidone, piperidinium, and imine.

* * * * *

UNITED STATES PATENT AND TRADEMARK OFFICE
CERTIFICATE OF CORRECTION

PATENT NO. : 12,172,153 B2
APPLICATION NO. : 16/970444
DATED : December 24, 2024
INVENTOR(S) : Andrew Tomlinson et al.

It is certified that error appears in the above-identified patent and that said Letters Patent is hereby corrected as shown below:

In the Claims

In Column 35, Claim 5, Line 57, delete "(a)" and insert -- ($\alpha$) --, therefor.

In Column 36, Claim 6, Line 3, delete "(a)" and insert -- ($\alpha$) --, therefor.

In Column 36, Claim 9, Line 14, delete "are is" and insert -- is --, therefor.

In Column 36, Claim 12, Line 31, delete "and least" and insert -- and at least --, therefor.

In Column 36, Claim 12, Line 32, delete "comprising;" and insert -- comprising: --, therefor.

Signed and Sealed this
Twenty-fifth Day of February, 2025

Coke Morgan Stewart
*Acting Director of the United States Patent and Trademark Office*